US009107945B2

(12) United States Patent
Hope et al.

(10) Patent No.: US 9,107,945 B2
(45) Date of Patent: Aug. 18, 2015

(54) METHODS OF PURIFYING ANTI-INTERLEUKIN-13 ANTIBODIES

(75) Inventors: Claire Louise Hope, Cambridge (GB); Karen Bannister, Cambridge (GB); Brendan Cormick Fish, Cambridge (GB); Jeanette Elizabeth Langstone, Cambridge (GB)

(73) Assignee: MedImmune Limited, Cambridge (GB)

( * ) Notice: Subject to any disclaimer, the term of this patent is extended or adjusted under 35 U.S.C. 154(b) by 1205 days.

(21) Appl. No.: 12/966,377

(22) Filed: Dec. 13, 2010

(65) Prior Publication Data
US 2011/0086038 A1 Apr. 14, 2011

Related U.S. Application Data

(63) Continuation of application No. 12/067,120, filed as application No. PCT/GB2006/003650 on Sep. 29, 2006, now abandoned.

(60) Provisional application No. 60/721,974, filed on Sep. 30, 2005.

(30) Foreign Application Priority Data

Sep. 30, 2005 (GB) .................................. 0519923.7

(51) Int. Cl.
*C07K 16/00* (2006.01)
*A61K 47/02* (2006.01)
*A61K 9/00* (2006.01)
*A61K 39/395* (2006.01)
*A61K 47/12* (2006.01)
*A61K 47/26* (2006.01)
*C07K 16/24* (2006.01)
*A61K 39/00* (2006.01)

(52) U.S. Cl.
CPC ............... *A61K 47/02* (2013.01); *A61K 9/0019* (2013.01); *A61K 39/39591* (2013.01); *A61K 47/12* (2013.01); *A61K 47/26* (2013.01); *C07K 16/244* (2013.01); *A61K 2039/505* (2013.01)

(58) Field of Classification Search
None
See application file for complete search history.

(56) References Cited

U.S. PATENT DOCUMENTS

| 5,596,072 | A | 1/1997 | Culpepper et al. |
| 5,652,123 | A | 7/1997 | Caput et al. |
| 2004/0197324 | A1 | 10/2004 | Liu et al. |
| 2004/0234499 | A1 | 11/2004 | Shealy et al. |
| 2004/0248260 | A1 | 12/2004 | Heavner et al. |
| 2005/0065327 | A1 | 3/2005 | Monk et al. |
| 2005/0158316 | A1 | 7/2005 | Lam et al. |

FOREIGN PATENT DOCUMENTS

| EP | 1616881 A1 | 1/2006 |
| FR | 2685919 A1 | 9/1993 |
| WO | WO9217586 | 10/1992 |
| WO | WO9745140 | 12/1997 |
| WO | WO9856418 A1 | 12/1998 |
| WO | WO03035847 A2 | 1/2003 |
| WO | WO03086451 A1 | 10/2003 |
| WO | WO2004001007 A2 | 12/2003 |
| WO | WO2004076485 A1 | 10/2004 |
| WO | WO2005007699 A2 | 1/2005 |
| WO | WO2005081873 A2 | 9/2005 |

OTHER PUBLICATIONS

Ahlers, J. D. et al., "A push-pull approach to maximize vaccine efficacy: Abrogating suppression with an IL-13 inhibitor while augmenting help with granulocyte/macrophage colony-stimulating factor and CD40L," Proceedings of the National Academy of Sciences of the United States of America, 2002, vol. 99, No. 20, pp. 13020-13025.

Bagshawe, K.D. et al., "Antibody-Enzyme Conjugates Can Generate Cytotoxic Drugs from Inactive Precursors at Tumor Sites," Antibody, Immunoconjugates and Radiopharmaceuticals, 1991, vol. 4, pp. 915-922.

Fiumara, P. et al., "Interleukin-13 levels in serum from patients with Hodgkin disease and healthy volunteers," Blood, 2001, vol. 98, No. 9, pp. 2877-2878.

Graves, P. E. et al., "A cluster of seven tightly linked polymorphisms in the IL-13 gene is associated with total serum IgE levels in three populations of white children," The Journal of Allergy and Clinical Immunology, Mar. 2000, vol. 105, No. 3, pp. 506-513.

Grunig, G. et al., "Requirement for IL-13 Independently of IL-4 in Experimental Asthma," Science, Dec. 18, 1998, vol. 282, No. 5397, pp. 2261-2263.

Hancock, A. et al., "Production of interleukin 13 by alveolar macrophages from normal and fibrotic lung," American Journal of Respiratory Cell and Molecular Biology, 1998, vol. 18, No. 1, pp. 60-65.

Hasegawa, M. et al., "Elevated serum levels of interleukin 4 (IL-4), IL-10, and IL-13 in patients with systemic sclerosis," The Journal of Rheumatology, 1997, vol. 24, No. 2, pp. 328-332.

Heinzmann, A. et al, "Genetic variants of IL-13 signalling and human asthma and atopy," Human Mol Genet, Mar. 1, 2000, vol. 9, No. 4, pp. 549-559.

Heller, F. et al., "Oxazolone colitis, a Th2 colitis model resembling ulcerative colitis, is mediated by IL-13-producing NK-T cells," Immunity, Nov. 2002, vol. 17, No. 5, pp. 629-638.

Howard, T. D. et al., "Gene-Gene Interaction in Asthma: IL4RA and IL13 in a Dutch Population with Asthma," The American Journal of Human Genetics, Jan. 2002, vol. 70, No. 1, pp. 230-236.

Kauppi, P. et al., "A Second-Generation Association Study of the 5q31 Cytokine Gene Cluster and the Interleukin-4 Receptor in Asthma," Genomics, Sep. 2001, vol. 77, No. 1-2, pp. 35-42.

(Continued)

*Primary Examiner* — Yunsoo Kim

(57) ABSTRACT

The invention relates to a pharmaceutical composition comprising an interleukin-13 antibody, more particularly a monoclonal interleukin-13 antibody, especially a human interleukin-13 monoclonal antibody, to a process for purifying said antibody and to the use of said composition in treating interleukin-13 related disorders, such as asthma, atopic dermatitis, allergic rhinitis, fibrosis, chronic obstructive pulmonary disease, scleroderma, inflammatory bowel disease and Hodgkin's lymphoma, particularly asthma.

14 Claims, 24 Drawing Sheets

(56) References Cited

OTHER PUBLICATIONS

Mckenzie, A.N. et al., "Structural comparison and chromosomal localization of the human and mouse IL-13 genes," The Journal of Immunology, Jun. 15, 1993, vol. 150, No. 12, pp. 5436-5444.

Minty, A. et al., "Interleukin-13 is a new human lymphokine regulating inflammatory and immune responses," Nature, Mar. 18, 1993, No. 362, Issue 6417, pp. 248-250.

Morse, B. et al., "Effects of IL-13 on airway responses in the guinea pig," American Journal of Physiology—Lung Cellular and Molecular Physiology, Jan. 1, 2002, vol. 282, No. 1, pp. L44-L49.

Norrby-Teglund, et al., (1996), "Evidence for the presence of streptococcal-superantigen-neutralizing antibodies in normal polyspecific immunoglobulin G," Infection and Immunity, vol. 64, No. 12, p. 5395-5398.

Terabe, M. et al., "NKT cell-mediated repression of tumor or immunosurveillance by IL-13 and the IL-4R-STAT6 pathway," Nature Immunology, Dec. 2000, vol. 1, No. 6, pp. 515-520.

Van Der Pouw Kraan, T. C. et al., "An IL-13 promoter polymorphism associated with increased risk of allergic asthma," Genes and Immunity, 1999, vol. 1, pp. 61-65.

Venkayya, R., et al., "The Th2 lymphocyte products IL-4 and IL-13 rapidly induce airway hyperresponsiveness through direct effects on resident airway cells," American Journal of Respiratory Cell and Molecular Biology, Feb. 2002, vol. 26, No. 2, pp. 202-208.

Wills-Karp, M. et al., "Interleukin-13: central mediator of allergic asthma," Science, Dec. 18, 1998, vol. 282, No. 5397, pp. 2258-2261.

Zheng, T. et al., "Inducible targeting of IL-13 to the adult lung causes matrix metalloproteinase- and cathepsin-dependent emphysema," The Journal of Clinical Investigation, Nov. 1, 2000, vol. 106, No. 9, pp. 1081-1093.

Zhu, Z. et al., "Pulmonary expression of interleukin-13 causes inflammation, mucus hypersecretion, subepithelial fibrosis, physiologic abnormalities, and eotaxin production," The Journal of Clinical Investigation, Mar. 15, 1999, vol. 103, No. 6, pp. 779-788.

International Search Report and Written Opinion for International Application No. PCT/GB2006/003650, European Patent Office mailed May 29, 2007.

International Preliminary Report on Patentability for International Application No. PCT/GB2006/003650, European Patent Office mailed Apr. 1, 2008.

FIGURE 1: Results of 28 Day SDS-PAGE Analysis at Day One
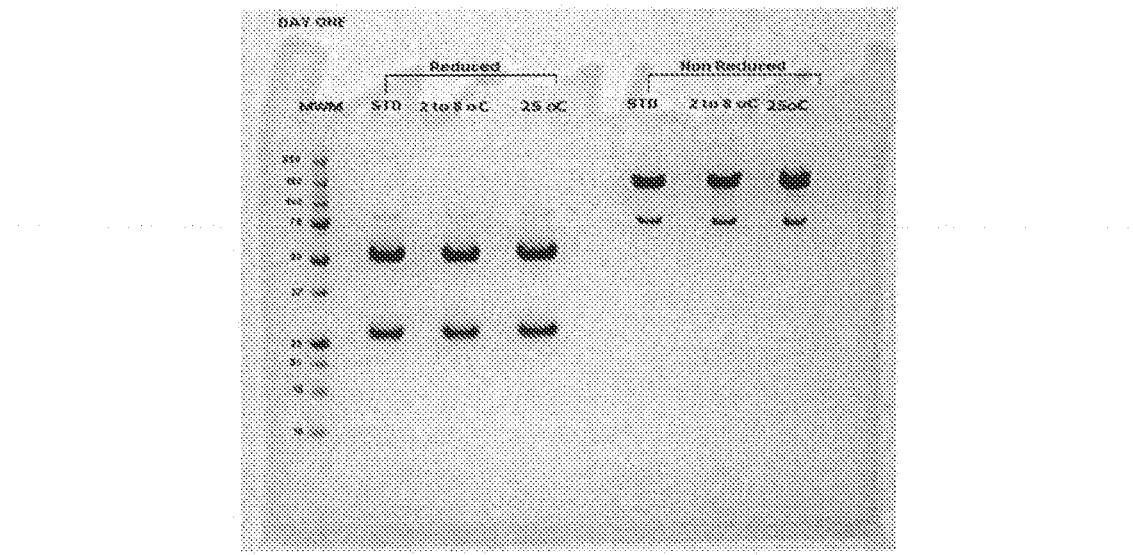
FIGURE 2: Results of 28 Day SDS-PAGE Analysis at Day Twenty One
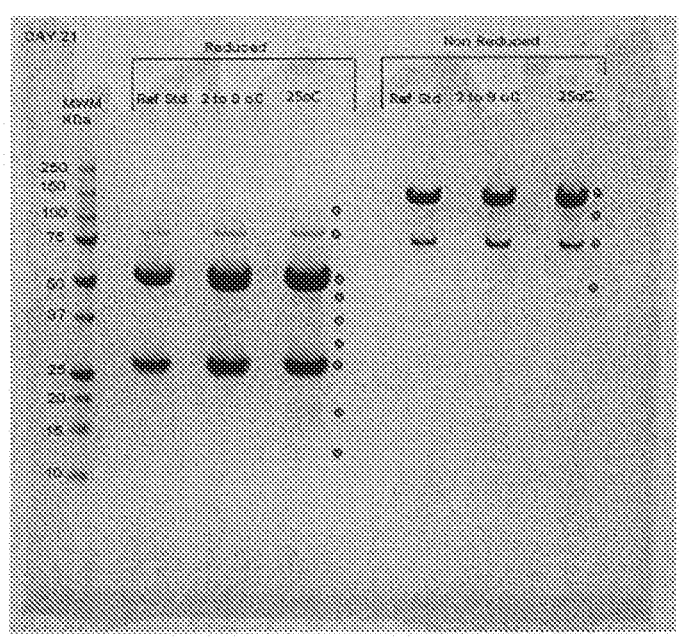

FIGURE 3: Day One Chromatograms from 28 Day GP-HPLC analysis of Protein A fractions
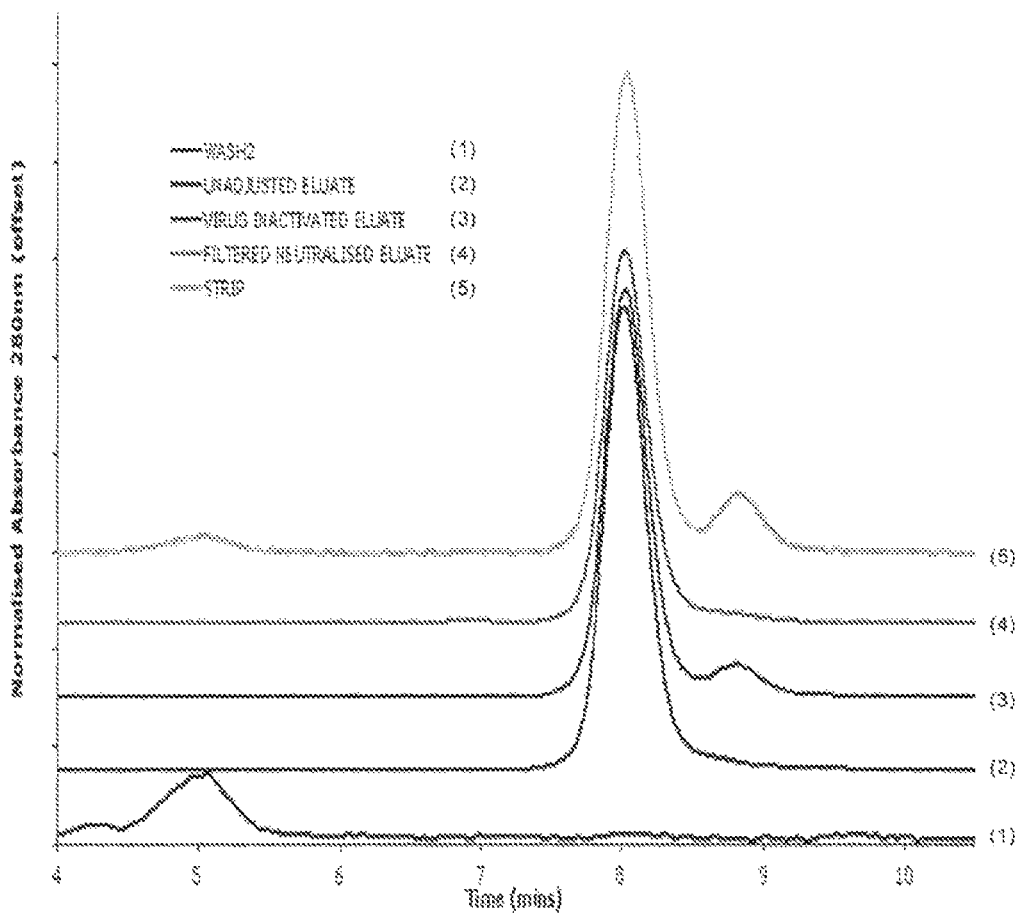

FIGURE 4: Magnification of chromatograms from 28 Day GP-HPLC analysis of eluates stored at 2 to 8°C.
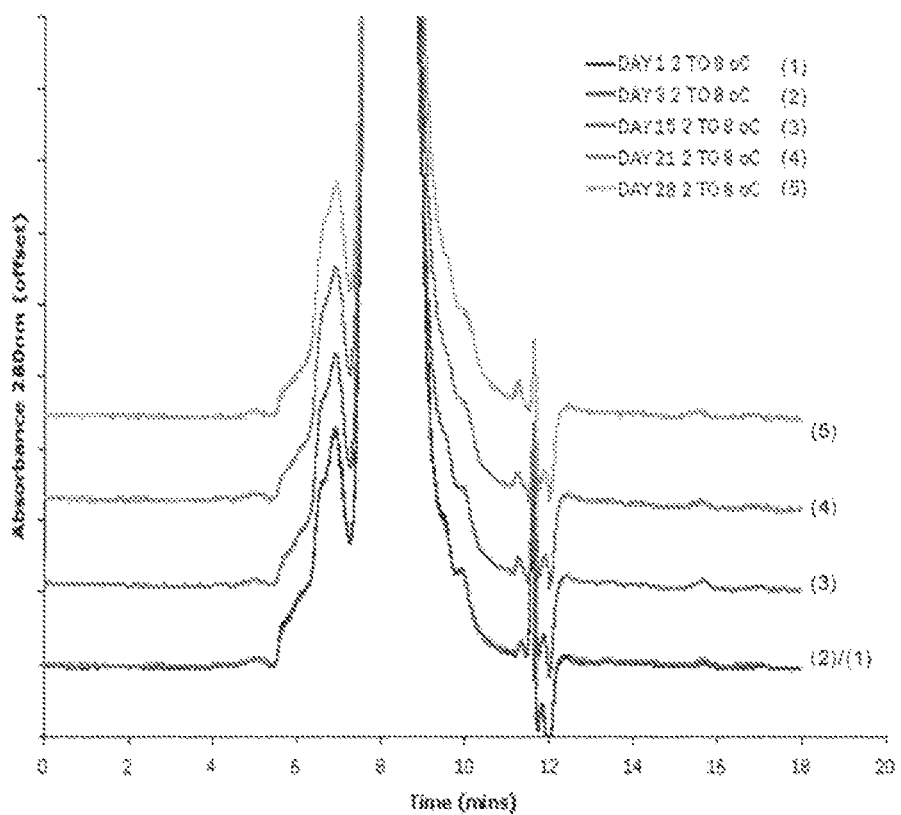

FIGURE 5: Magnification of chromatograms from 28 Day GP-HPLC analysis of eluates stored at 25°C.
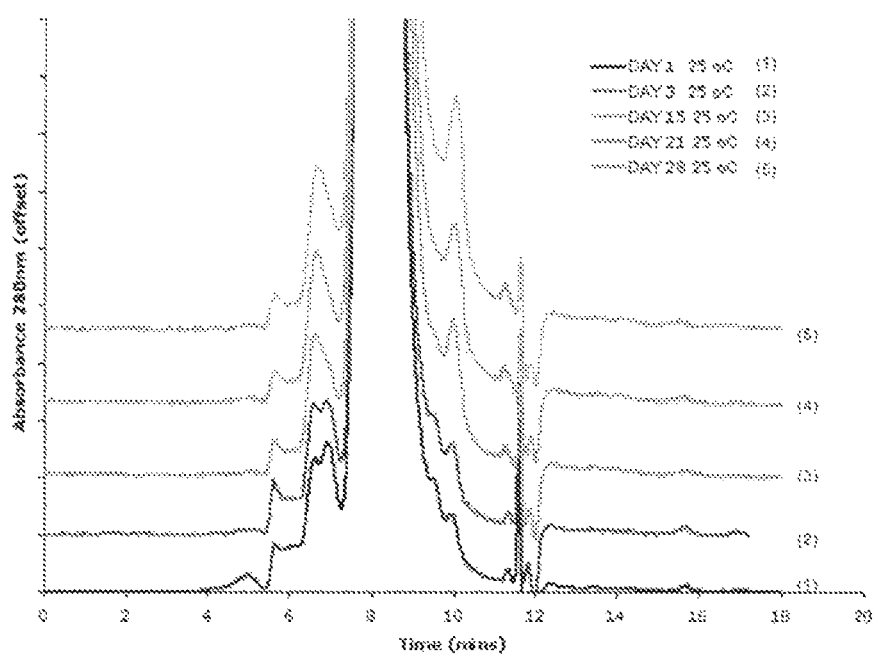

FIGURE 6: Magnification of chromatograms from 28 Day GP-HPLC analysis eluates neutralised with either 100mM or 50mM sodium hydroxide
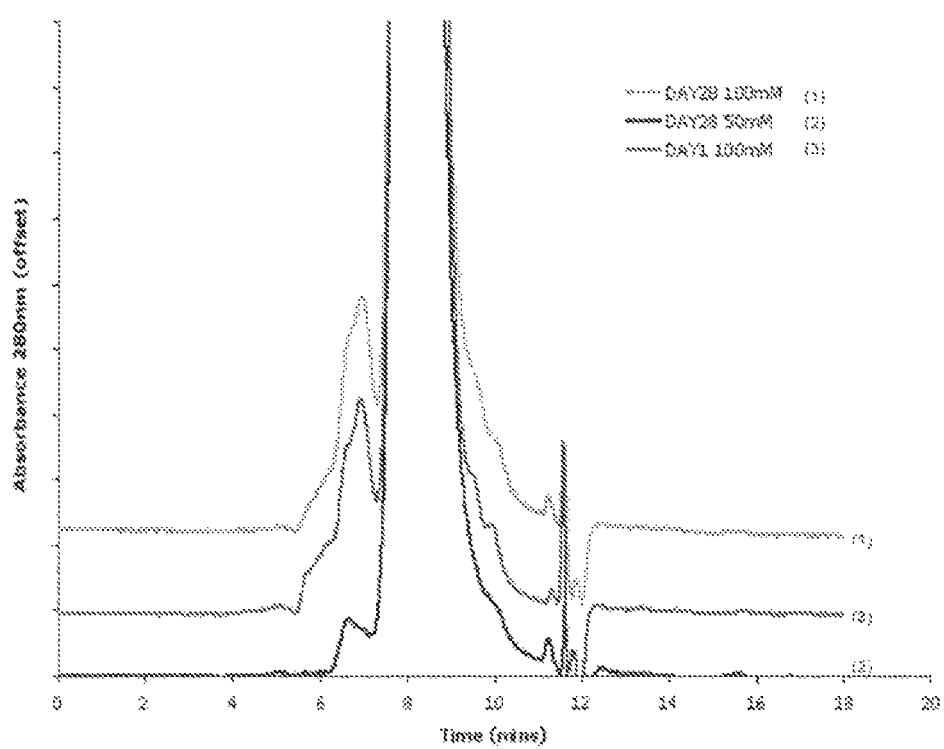

FIGURE 7: 28 Day IEF Analysis at Day Twenty Eight
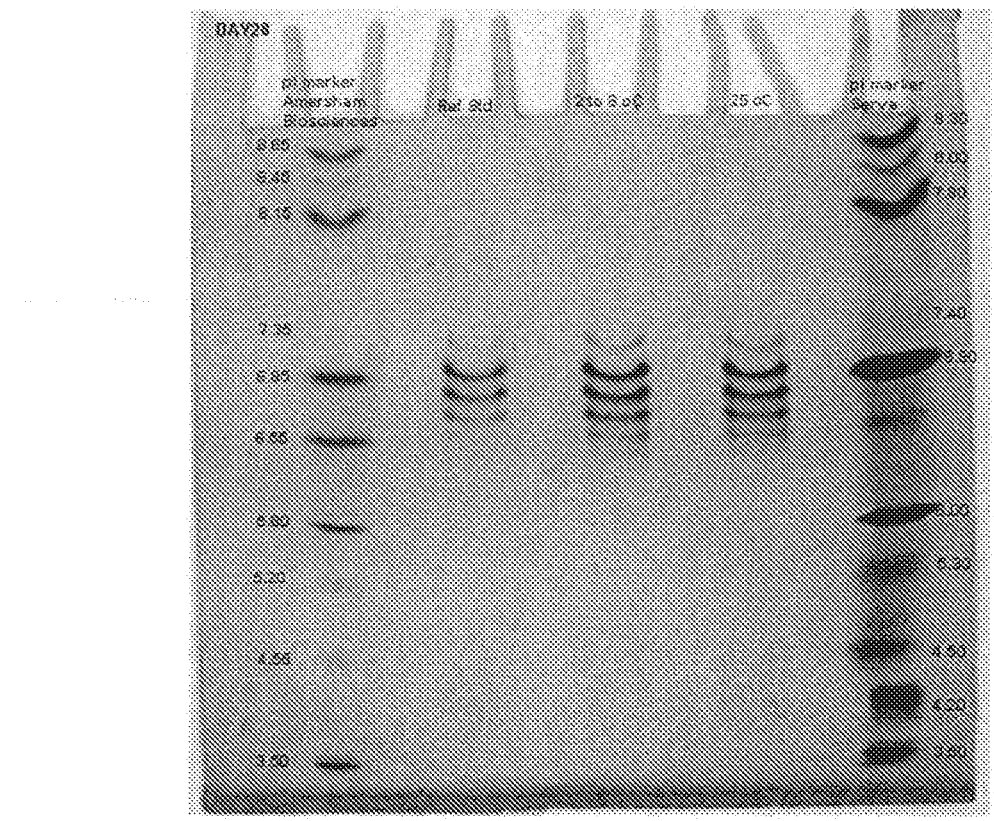
FIGURE 8: 12 Month Gel Filtration HPLC Analysis when stored at ~70°C
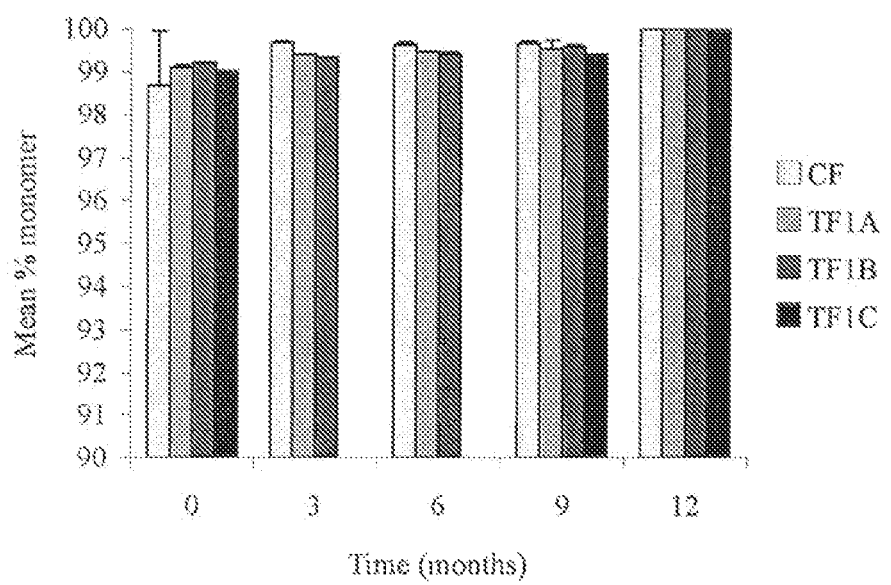

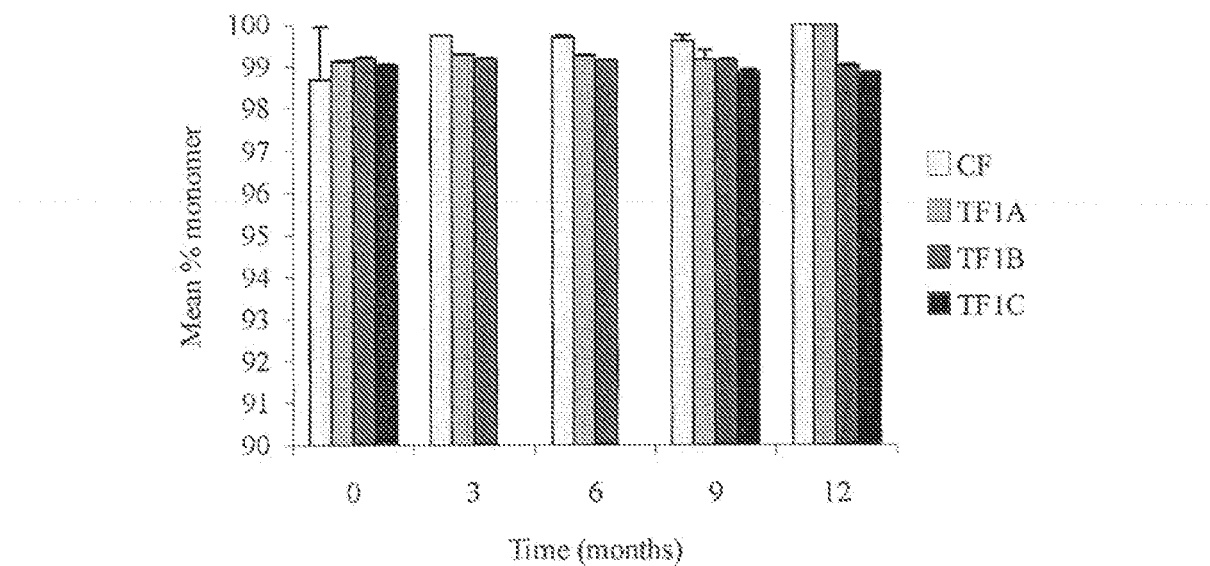
FIGURE 9: 12 Month Gel Filtration HPLC Analysis when stored at +5°C
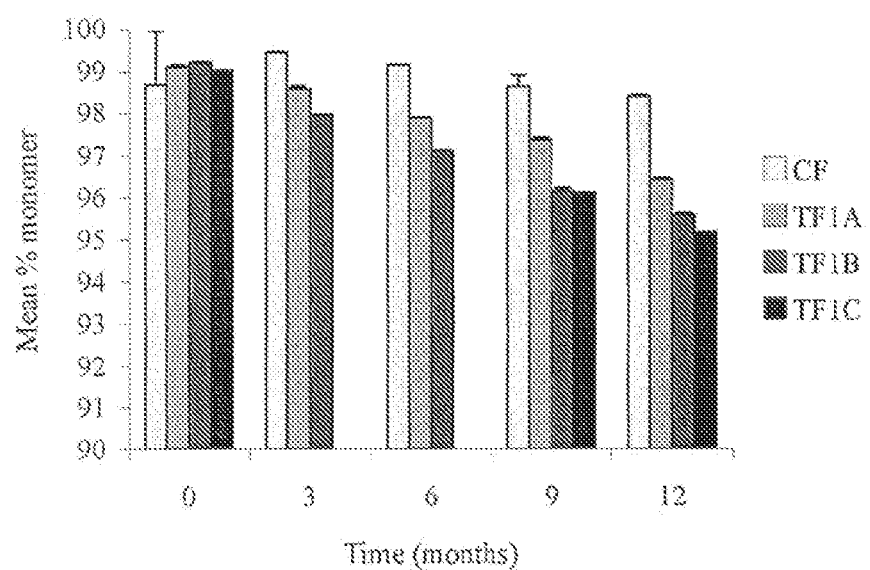
FIGURE 10: 12 Month Gel Filtration HPLC Analysis when stored at +25°C FIGURE 11: 8 Week Gel Filtration HPLC Analysis when stored at +37°C
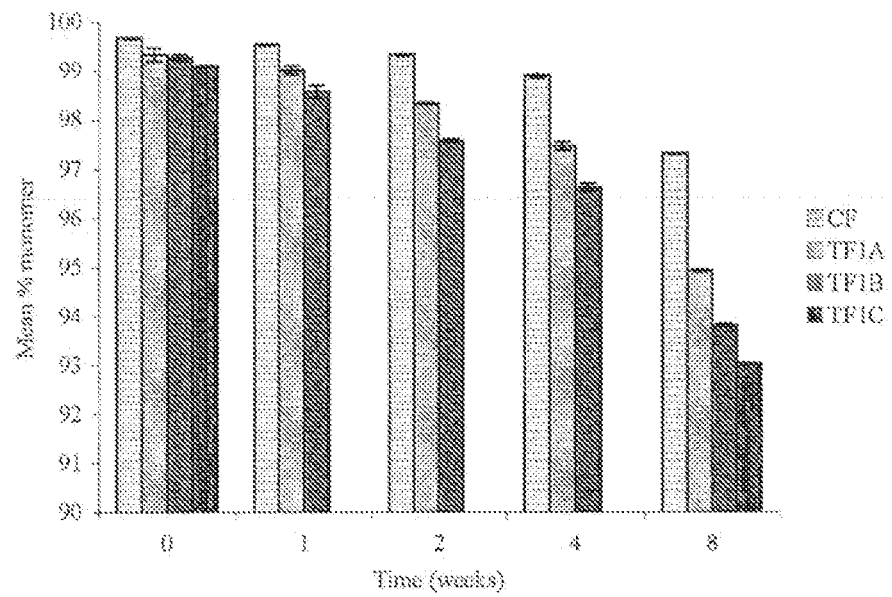
FIGURE 12: 5 Day Gel Filtration HPLC Analysis when stored at +45°C
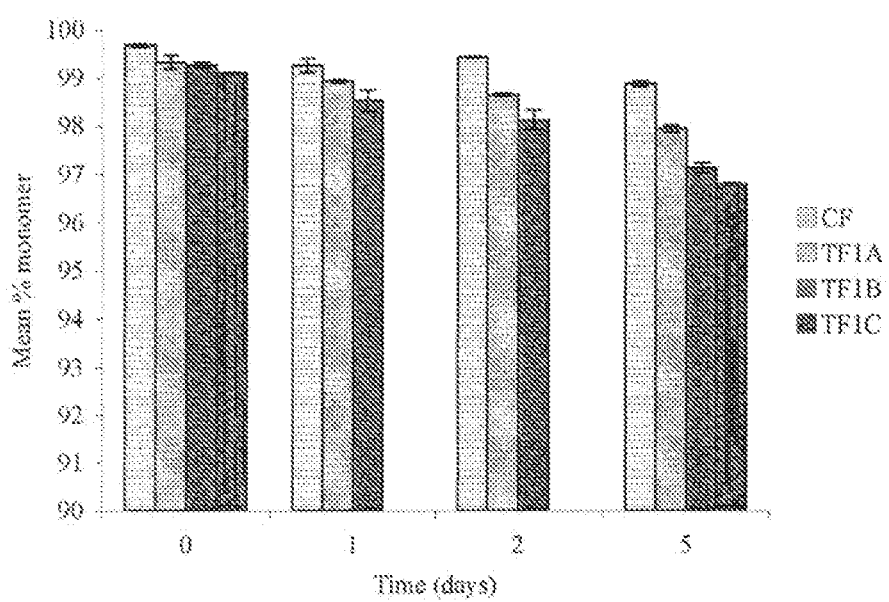

FIGURE 13: Reduced SDS-PAGE Analysis of samples at 0, 6 and 12 months when stored at -70°C
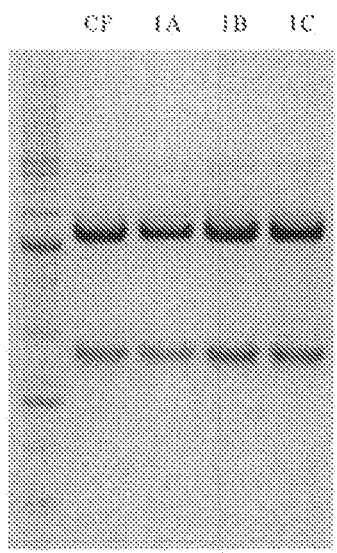
Time = 0
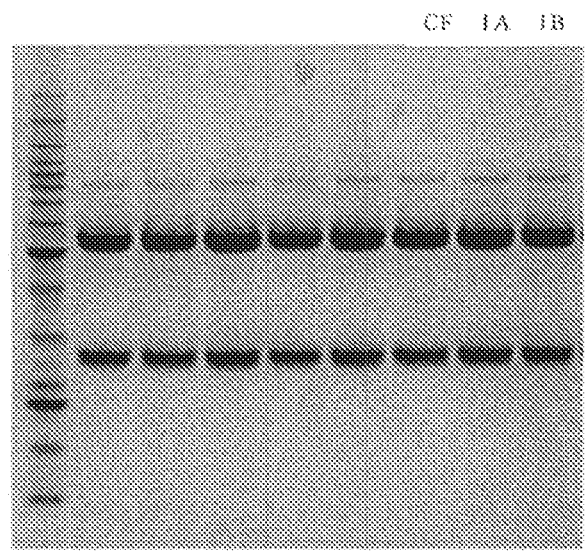
6 months at -70°C
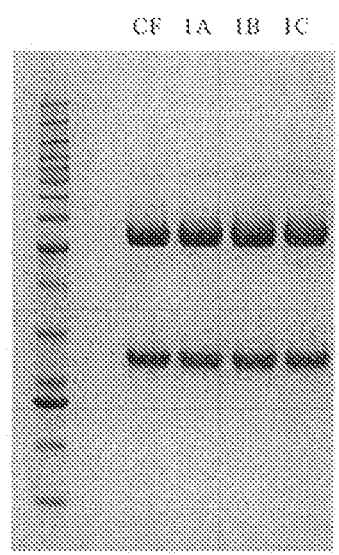
12 months at -70°C

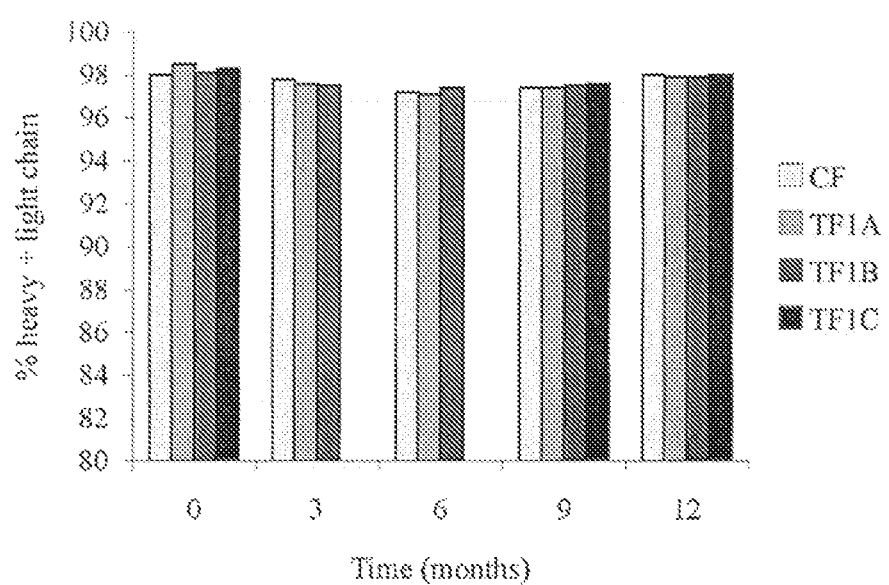
FIGURE 14: Percentage Abundance of BAK502G9 heavy and light chains following Reduced SDS-PAGE Analysis when stored at -70°C FIGURE 15: Reduced SDS-PAGE Analysis of samples at 0, 6 and 12 months when stored at +5°C
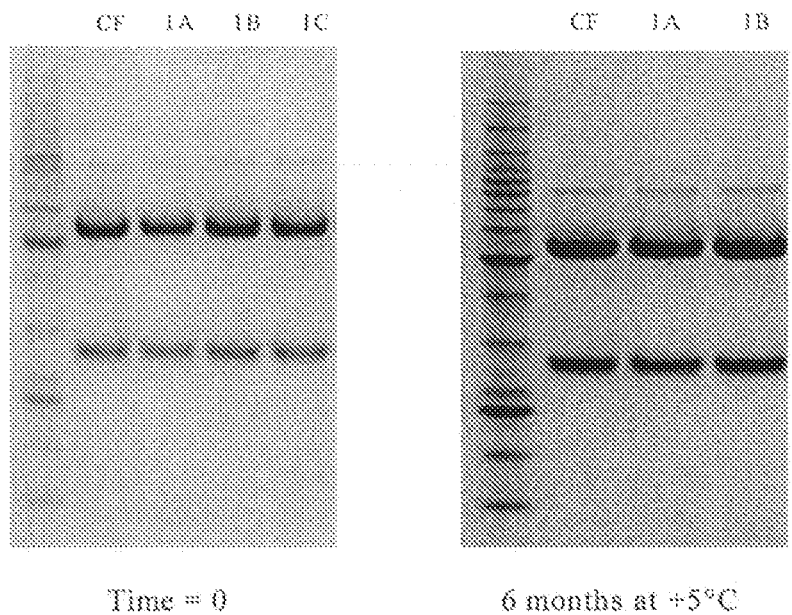
Time = 0
6 months at +5°C
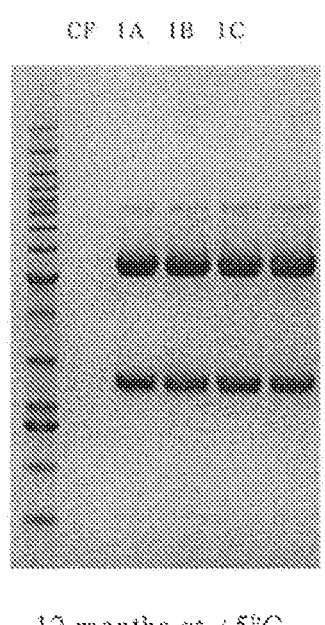
12 months at +5°C FIGURE 16: Percentage Abundance of BAK502G9 heavy and light chains following Reduced SDS-PAGE Analysis when stored at +5°C
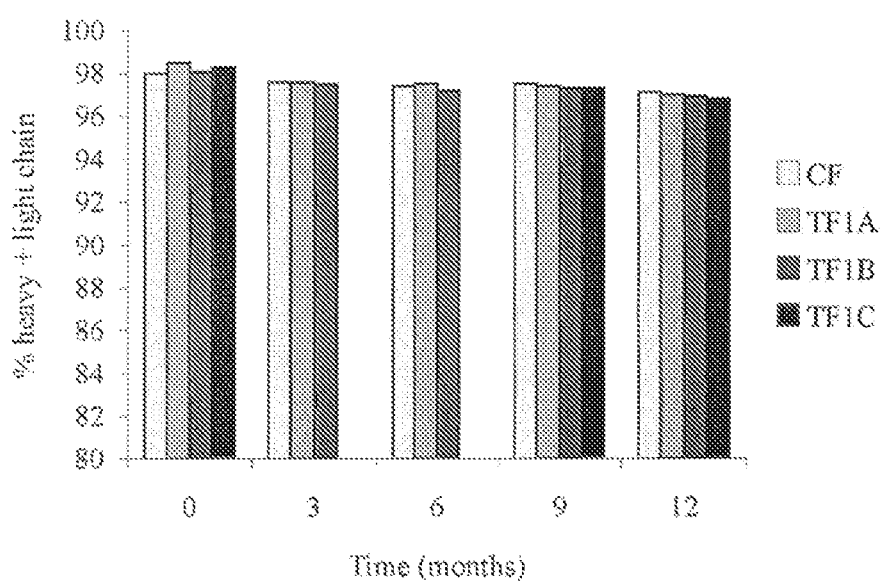

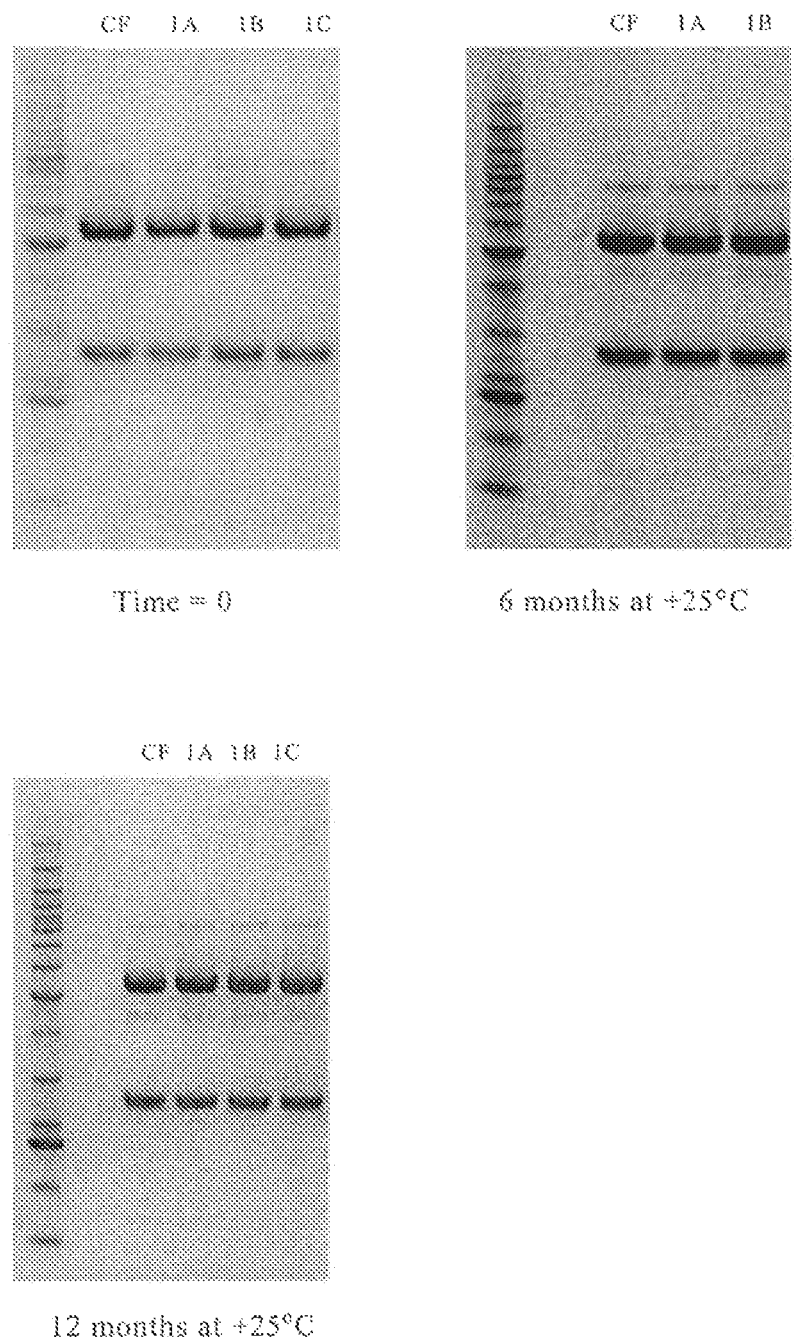
FIGURE 17: Reduced SDS-PAGE Analysis of samples at 0, 6 and 12 months when stored at +25°C FIGURE 18: Percentage Abundance of BAK502G9 heavy and light chains following Reduced SDS-PAGE Analysis when stored at +25°C
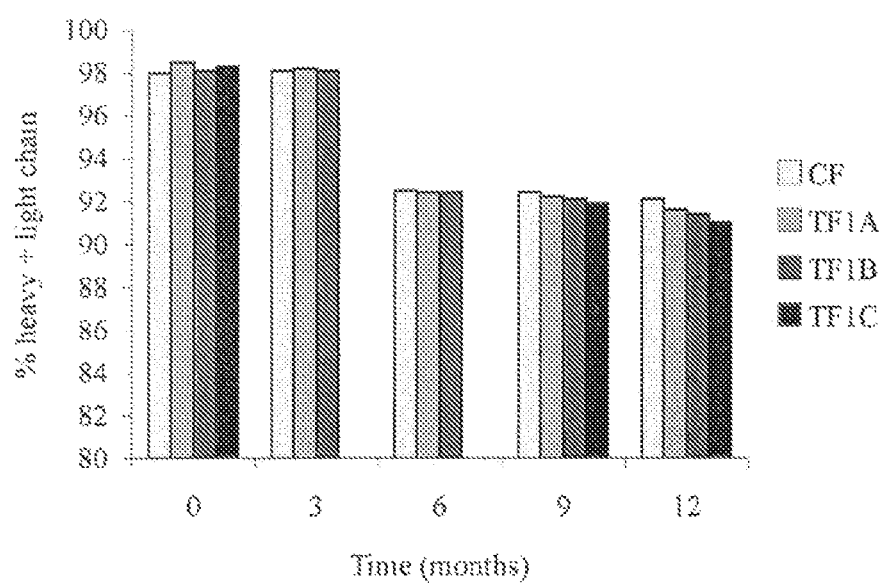

FIGURE 19: Reduced SDS-PAGE Analysis of samples at 0 and 8 weeks when stored at +37°C
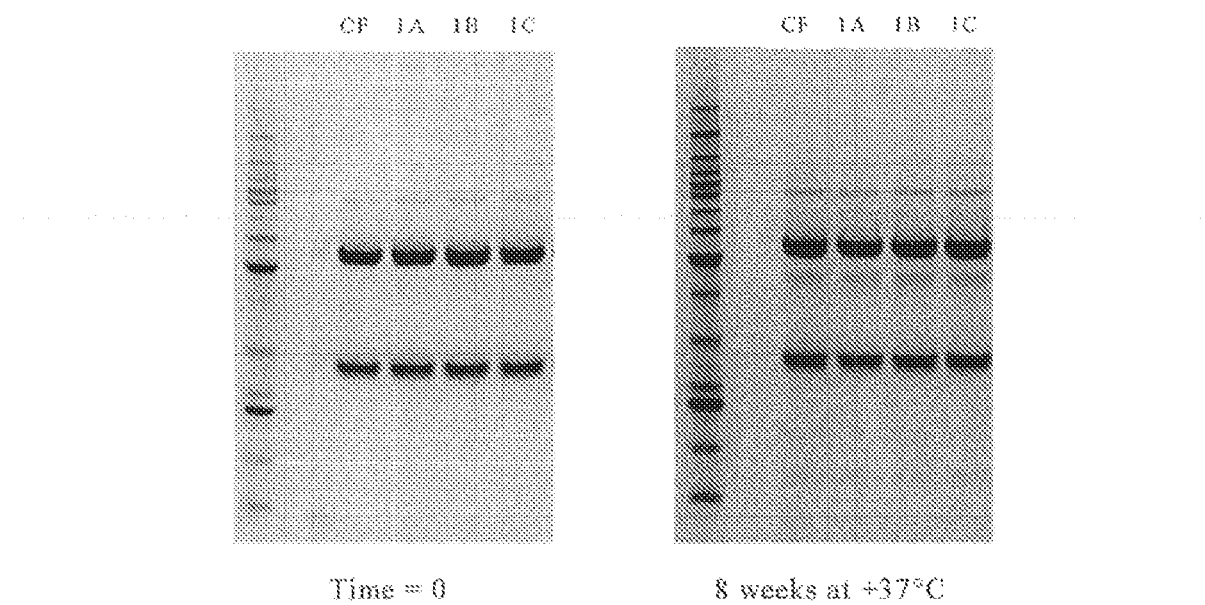
FIGURE 20: Percentage Abundance of BAK502G9 heavy and light chains following Reduced SDS-PAGE Analysis when stored at +37°C
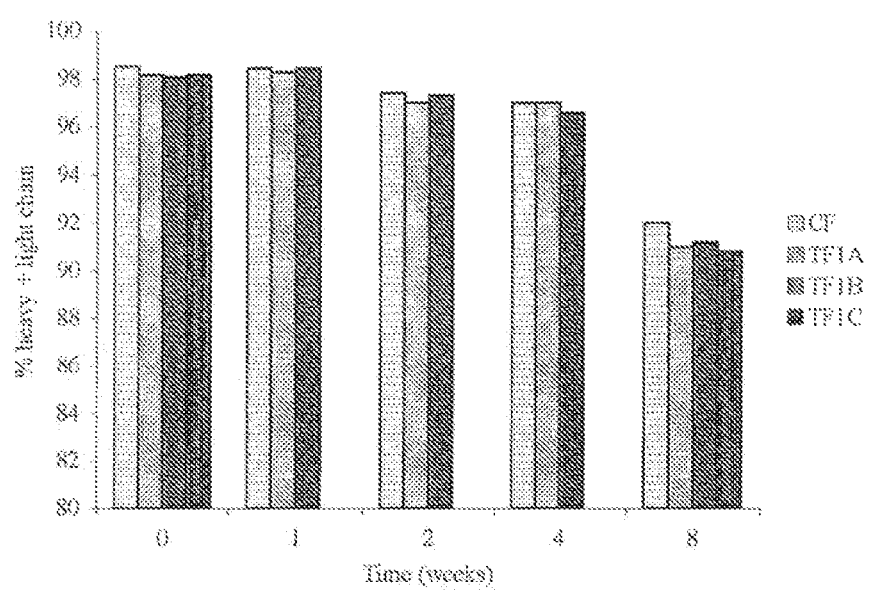

FIGURE 21: Reduced SDS-PAGE Analysis of samples at 0 and 5 days when stored at +45°C
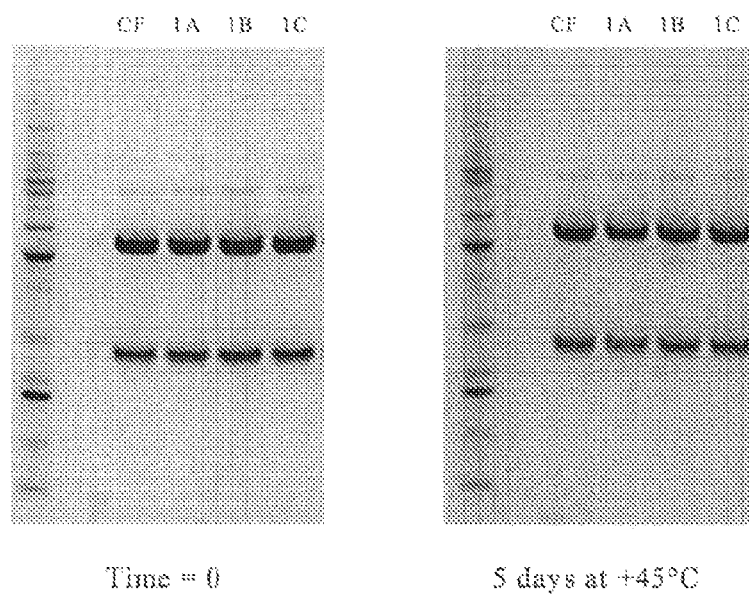
FIGURE 22: Percentage Abundance of BAK502G9 heavy and light chains following Reduced SDS-PAGE Analysis when stored at +45°C
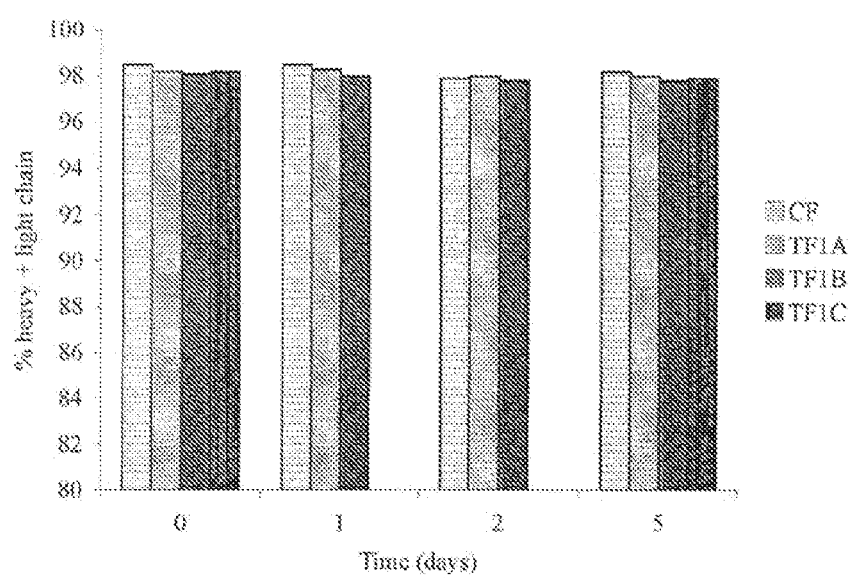

FIGURE 23: Non-Reduced SDS-PAGE Analysis of samples at 0, 6 and 12 months when stored at -70°C
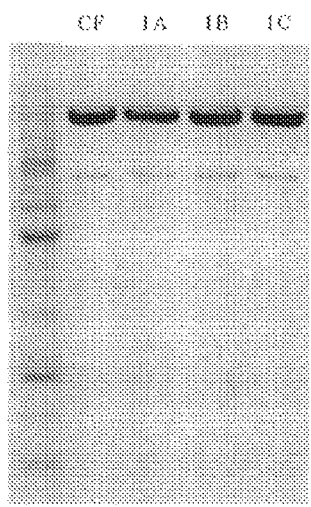
Time = 0
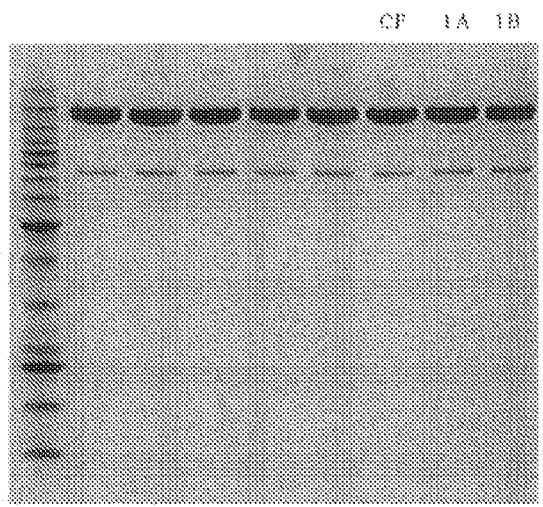
6 months at -70°C
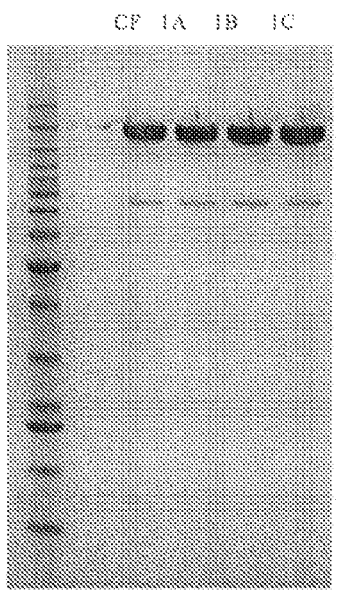
12 months at -70°C FIGURE 24: Percentage abundance of intact BAK502G9 monomer following Non-Reduced SDS-PAGE Analysis when stored at -70°C
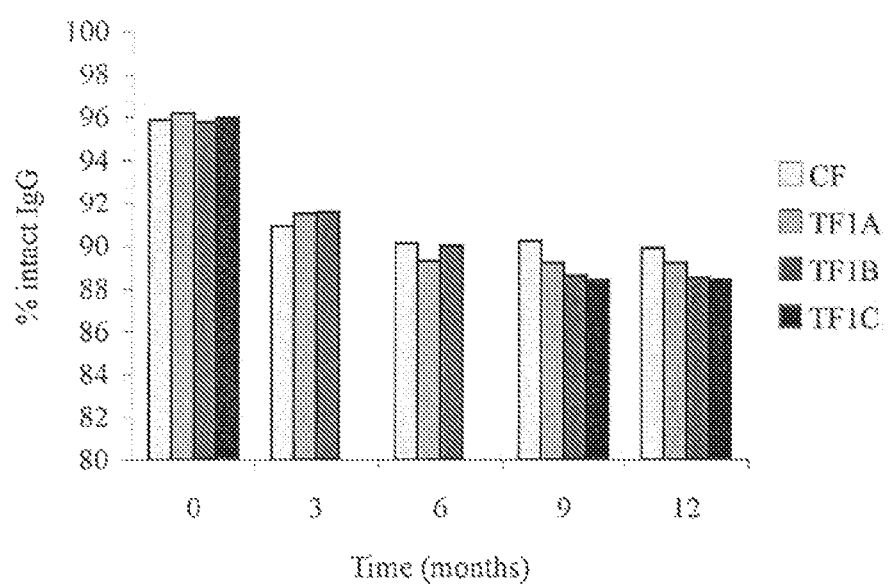

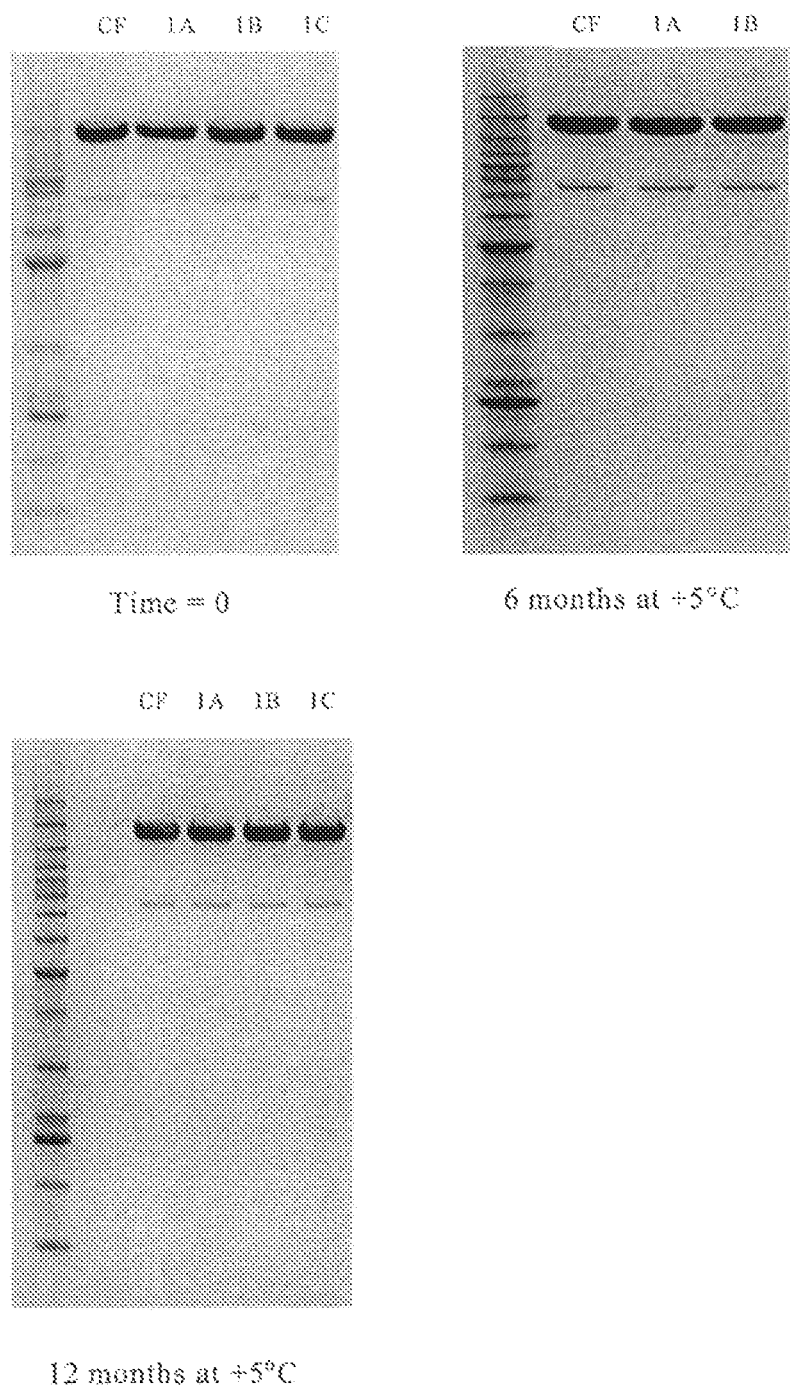
FIGURE 25: Non-Reduced SDS-PAGE Analysis of samples at 0, 6 and 12 months when stored at +5°C

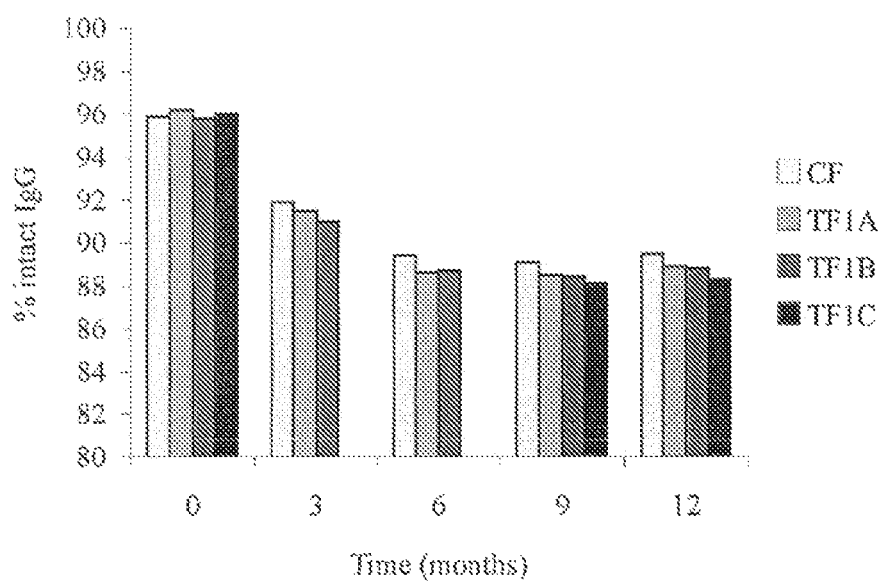
FIGURE 26: Percentage abundance of intact BAK502G9 monomer following Non-Reduced SDS-PAGE Analysis when stored at +5°C

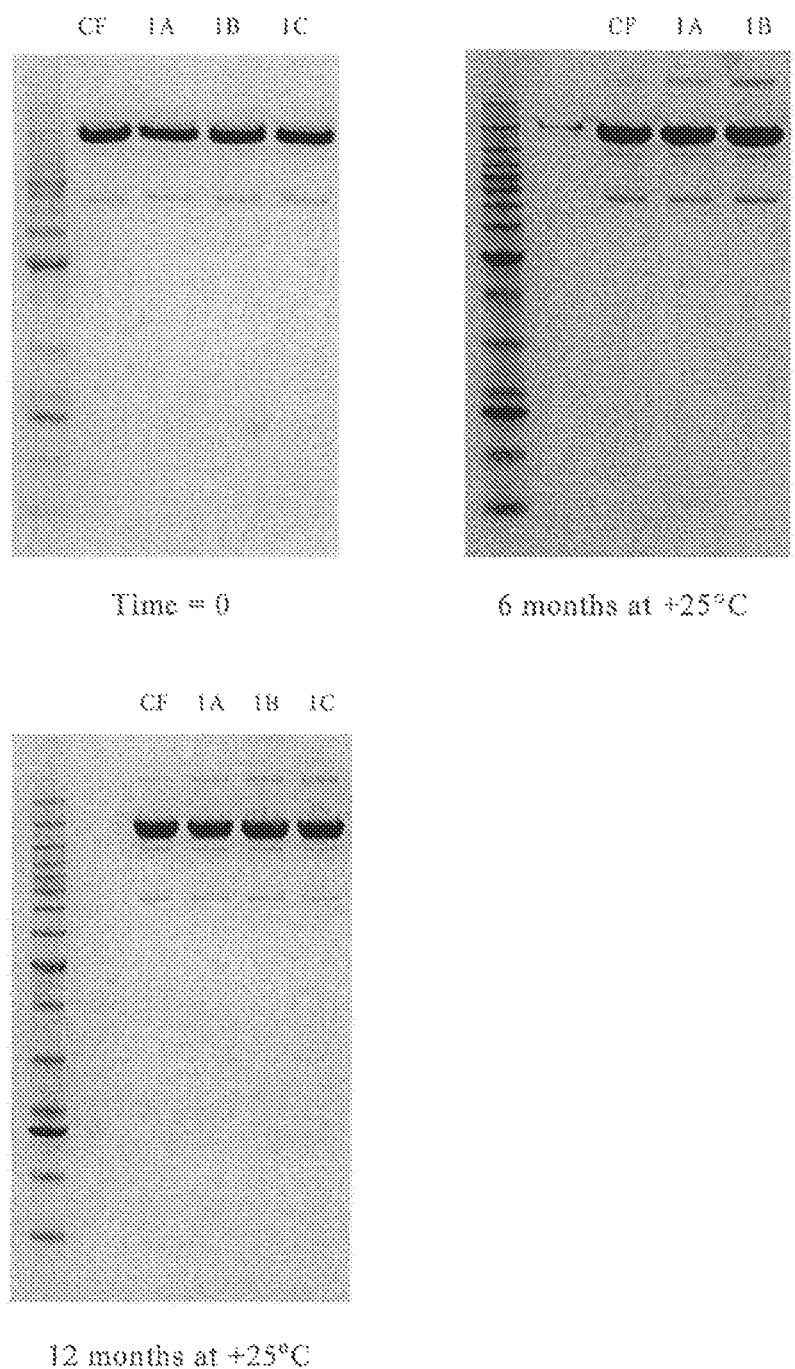

FIGURE 28: Percentage abundance of intact BAK502G9 monomer following Non-Reduced SDS-PAGE Analysis when stored at +25°C
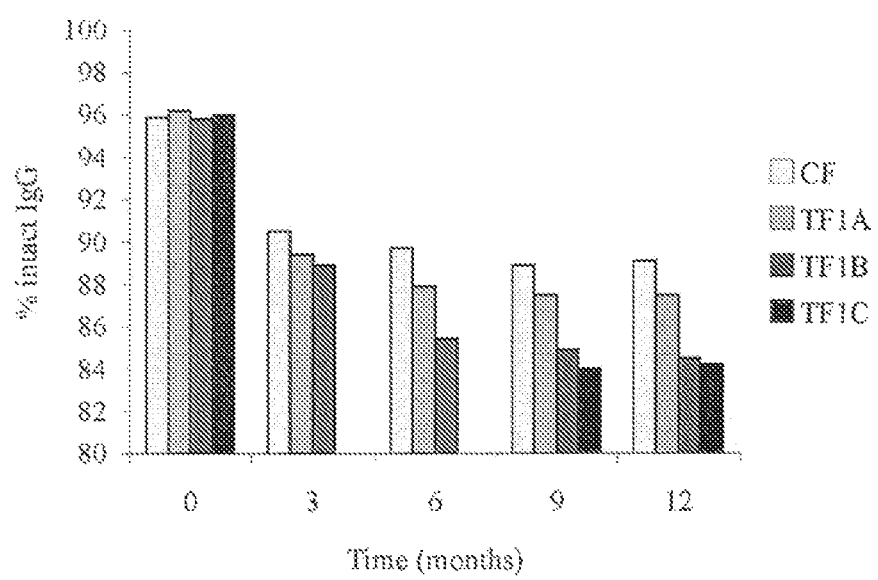

FIGURE 29: Non-Reduced SDS-PAGE Analysis of samples at 0 and 8 weeks when stored at +37°C
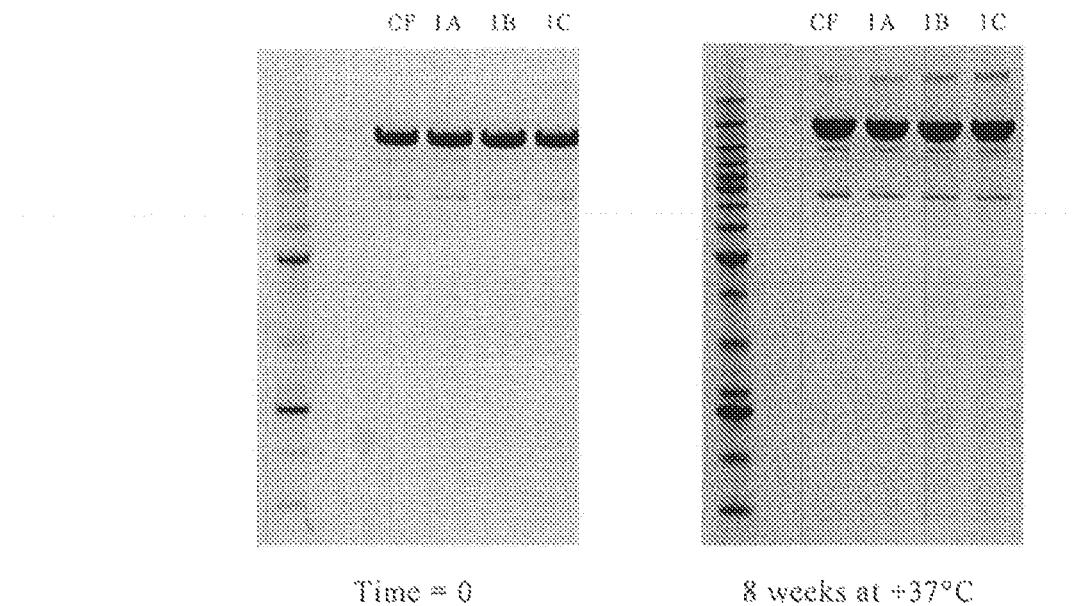
FIGURE 30: Percentage abundance of intact BAK502G9 monomer following Non-Reduced SDS-PAGE Analysis when stored at +37°C
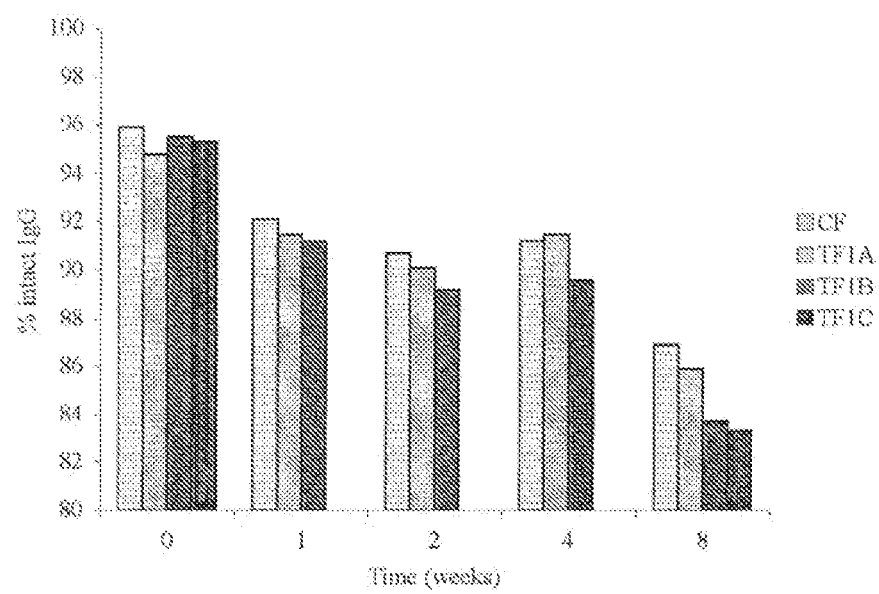

FIGURE 31: Non-Reduced SDS-PAGE Analysis of samples at 0 and 5 days when stored at +45°C
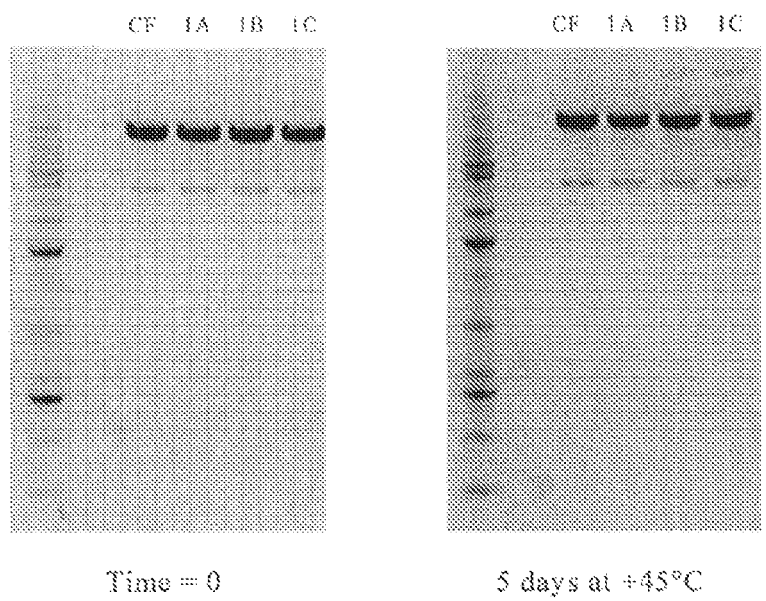
FIGURE 32: Percentage abundance of intact BAK502G9 monomer following Non-Reduced SDS-PAGE Analysis when stored at +45°C
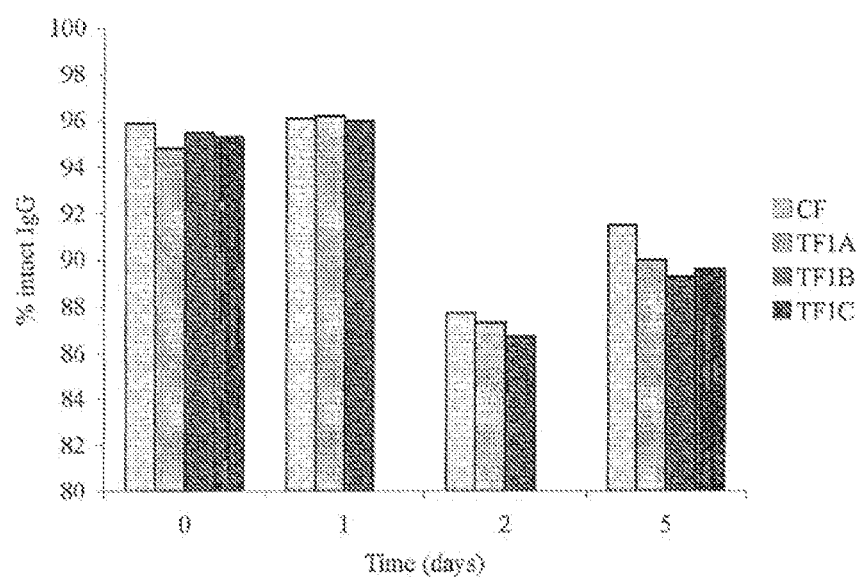

METHODS OF PURIFYING ANTI-INTERLEUKIN-13 ANTIBODIES

CROSS-REFERENCE TO RELATED APPLICATIONS

This application is a continuation of U.S. application Ser. No. 12/067,120, filed on Sep. 29, 2006, said application Ser. No. 12/067,120 is a National Phase filing of PCT/GB2006/003650 filed on Sep. 29, 2006 said Application No. PCT/GB2006/003650 claims benefit under 35 U.S.C. §119(e) and §365(b) of U.S. Provisional Application No. 60/721,974, filed on Sep. 30, 2005 and GB Application No. 0519923.7, filed on Sep. 30, 2005; each of the above-listed applications is incorporated by reference herein in its entirety for all purposes.

REFERENCE TO SEQUENCE LISTING SUBMITTED ELECTRONICALLY

The content of the electronically submitted sequence listing in ASCII text file (Name IL13-300US2_SL.txt; Size: 9,985 bytes; and Date of Creation: Sep. 15, 2014) is hereby incorporated by reference in its entirety.

The invention relates to a pharmaceutical composition comprising an interleukin-13 antibody, more particularly a monoclonal interleukin-13 antibody, especially a human interleukin-13 monoclonal antibody, to a process for purifying said antibody and to the use of said composition in treating interleukin-13 related disorders, such as asthma.

Interleukin (IL)-13 is a 114 amino acid cytokine with an unmodified molecular mass of approximately 12 kDa. IL-13 is most closely related to IL-4 with which it shares 30% sequence homology at the amino acid level. The human IL-13 gene is located on chromosome 5q31 adjacent to the IL-4 gene [McKenzie, A. N. et al., J Immunol, 1993. 150(12), 5436-5444; Minty, A. et al., Nature, 1993. 362(6417), 248-50].

Although initially identified as a Th2 CD4+ lymphocyte derived cytokine, IL-13 is also produced by Th1 CD4+ T-cells, CD8+ T lymphocytes NK cells, and non-T-cell populations such as mast cells, basophils, eosinophils, macrophages, monocytes and airway smooth muscle cells.

IL-13 has been linked with a number of diseases, in particular, diseases which are caused by an inflammatory response. For example, administration of recombinant IL-13 to the airways of naive non-sensitised rodents was shown to cause many aspects of the asthma phenotype including airway inflammation, mucus production and airways hyperresponsiveness (AHR) [Wills-Karp, M. et al., Science, 1998. 282(5397), 2258-2261; Grunig, G. et al., Science, 1998. 282 (5397), 2261-2263; Venkayya, R., et al., Am J Respir Cell Mol Biol, 2002. 26(2), 202-208; Morse, B. et al., Am J Physiol Lung Cell Mol Physiol, 2002. 282(1), L44-49]. A similar phenotype was observed in a transgenic mouse in which IL-13 was specifically overexpressed in the lung. In this model, more chronic exposure to IL-13 also resulted in fibrosis [Zhu, Z. et al., J Clin Invest, 1999. 103(6), 779-788].

A number of genetic polymorphisms in the IL-13 gene have also been linked to allergic diseases. In particular, a variant of the IL-13 gene in which the arginine residue at amino acid 130 is substituted with glutamine (Q130R) has been associated with bronchial asthma, atopic dermatitis and raised serum IgE levels [Heinzmann, A. et al., Hum Mol Genet, 2000. 9(4), 549-559; Howard, T. D. et al., Am J Hum Genet, 2002. 70(1), 230-236; Kauppi, P. et al., Genomics, 2001. 77(1-2), 35-42; Graves, P. E. et al., J Allergy Clin Immunol, 2000. 105(3), 506-513]. This particular IL-13 variant is also referred to as the Q110R variant (arginine residue at amino acid 110 is substituted with glutamine) by some groups who exclude the 20 amino acid signal sequence from the amino acid count.

IL-13 production has also been associated with allergic asthma [van der Pouw Kraan, T. C. et al., Genes Immun, 1999. 1(1), 61-65] and raised levels of IL-13 have been measured in human subjects with atopic rhinitis (hay fever), allergic dermatitis (eczema) and chronic sinusitis.

Aside from asthma, IL-13 has been associated with other fibrotic conditions. Increased levels of IL-13, up to a 1000 fold higher than IL-4, have been measured in the serum of patients with systemic sclerosis and in broncho-alveolar lavage (BAL) samples from patients affected with other forms of pulmonary fibrosis [Hasegawa, M. et al., J Rheumatol, 1997. 24(2), 328-332; Hancock, A. et al., Am J Respir Cell Mol Biol, 1998. 18(1), 60-65].

It has been demonstrated that overexpression of IL-13 in the mouse lung caused emphysema, elevated mucus production and inflammation, reflecting aspects of human chronic obstructive pulmonary disease (COPD) [Zheng, T. et al., J Clin Invest, 2000. 106(9), 1081-1093].

It has been proposed that IL-13 may also play a role in the pathogenesis of inflammatory bowel disease [Heller, F. et al., Immunity, 2002. 17(5), 629-38] and raised levels of IL-13 have been detected in the serum of some Hodgkin's disease patients when compared to normal controls [Fiumara, P. et al., Blood, 2001. 98(9), 2877-2878].

IL-13 inhibitors are also believed to be therapeutically useful in the prevention of tumour recurrence or metastasis [Terabe, M. et al., Nat Immunol, 2000. 1(6), 515-520]. Inhibition of IL-13 has also been shown to enhance anti-viral vaccines in animal models and may be beneficial in the treatment of HIV and other infectious diseases [Ahlers, J. D. et al., Proc Natl Acad Sci USA, 2002. 99(20), 13020-13025].

An antibody directed approach to IL-13 inhibition has been described. For example, WO 2005/007699 (Cambridge Antibody Technology Limited) describes a series of human anti-IL-13 antibody molecules which are shown to neutralise IL-13 activity and which are claimed to be of potential use in the treatment of IL-13 related disorders.

According to a first aspect of the invention there is provided a pharmaceutical composition comprising an IL-13 antibody and one or more pharmaceutically acceptable excipients buffered to a pH of 4.5-6.0 with acetate buffer.

It is commonly known that antibody purification procedures typically require a number of separation techniques, such as chromatography separations (e.g. Protein A chromatography, ion exchange chromatography and the like). A consequence of this manner of separation requires the use of a number of differing buffers. For example, the antibody purification procedure described in WO 2004/076485 requires the use of 50 mM glycine/glycinate pH 8.0 for Protein A chromatography, 50 mM TrisHCl pH 8.0 and 20 mM sodium phosphate pH 6.5 for Q-Sepharose chromatography, and 25 mM TrisHCl pH 8.6 for DEAE-sepharose chromatography.

By contrast, the present invention requires the use of a single acetate buffer at a fixed concentration and predetermined pH present within the composition of the invention which has the advantage of being present throughout all IL-13 antibody purification steps. Thus, the use of this buffer, not only at the beginning of the purification process, but throughout the entire purification process, therefore results in a reduction of processing time, cost and an increase in product yield.

It will be appreciated that references to "antibody" include references to an immunoglobulin whether natural or partly or wholly synthetically produced. The term also covers any polypeptide or protein comprising an antigen binding domain.

Antibody fragments which comprise an antigen binding domain are molecules such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB2188638A or EP-A-239400, and a large body of subsequent literature.

Alternatively, novel VH or VL regions carrying CDR-derived sequences may be generated using random mutagenesis of one or more selected VH and/or VL genes to generate mutations within the entire variable domain. Such a technique is described by Gram et al., PNAS USA, 1992. 89, 3576-3580, who use error prone PCR. Another method which may be used is to direct mutagenesis to CDR regions of VH and VL genes. Such techniques are disclosed by Barbas et al., PNAS USA 1994. 91, 3809-3813 and Schier et al., J. Mol. Biol. 1996. 263, 551-567.

As antibodies can be modified in a number of ways, the term "antibody" should be construed as covering any specific binding member or substance having an antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann et al., [2001; Antibody Engineering, Springer Laboratory Manuals]. Phage display, another established technique for generating specific binding members has been described in detail in many publications such as Kontermann et al. (supra) and WO92/01047. Transgenic mice in which the mouse antibody genes are inactivated and functionally replaced with human antibody genes while leaving intact other components of the mouse immune system, can be used for isolating human antibodies to human antigens. Ribosome display, a cell free translation technology which introduces mutations into known gene sequences, may also be used to generate and/or optimise specific binding members [Hanes and Plückthun PNAS USA, 1994. 94, 4937-4942; He and Taussig Nucleic Acids Res. 1997. 25, 5132-5134; Schaffitzel et al., J. Immunol. Methods, 1999. 231, 119-135; He et al., J. Immunol. Methods, 1999. 231, 105-117; He et al., Methods Mol. Biol. 2004. 248, 177-189].

Synthetic antibody molecules may be created by expression from genes generated by means of oligonucleotides synthesized and assembled within suitable expression vectors, for example as described by Knappik et al., J. Mol. Biol. 2000. 296, 57-86 or Krebs et al., Journal of Immunological Methods 2001. 254, 67-84.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [Ward, E. S. et al., Nature, 1989. 341, 544-546; McCafferty et al., Nature, 1990. 348, 552-554; Holt et al., Trends Biotechnol. 2003. 21(11), 484-490] which consists of a VH or a VL domain; (v) isolated CDR regions; (vi) F(ab') 2 fragments, a bivalent fragment comprising two linked Fab fragments (vii) single chain Fv molecules (scFv), wherein a VH domain and a VL domain are linked by a peptide linker which allows the two domains to associate to form an antigen binding site [Bird et al., Science, 1988. 242, 423-426; Huston et al., PNAS USA, 1988. 85, 5879-5883]; (viii) bispecific single chain Fv dimers (PCT/US92/09965) and (ix) "diabodies", multivalent or multispecific fragments constructed by gene fusion [WO94/13804; P. Holliger et al., Proc. Natl. Acad. Sci. USA, 1993. 90, 6444-6448]. Fv, scFv or diabody molecules may be stabilised by the incorporation of disulphide bridges linking the VH and VL domains [Y. Reiter et al., Nature Biotech., 1996. 14, 1239-1245]. Minibodies comprising a scFv joined to a CH3 domain may also be made [S. Hu et al., Cancer Res., 1996. 56, 3055-3061].

Where bispecific antibodies are to be used, these may be conventional bispecific antibodies, which can be manufactured in a variety of ways [Holliger and Winter Current Opinion Biotechnol. 1993. 4, 446-449], e.g. prepared chemically or from hybrid hybridomas, or may be any of the bispecific antibody fragments mentioned above. Examples of bispecific antibodies include those of the BiTE technology in which the binding domains of two antibodies with different specificity can be used and directly linked via short flexible peptides. This combines two antibodies on a short single polypeptide chain. Diabodies and scFv can be constructed without an Fc region using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against IL-13, then a library can be made where the other arm is varied and an antibody of appropriate specificity selected. Bispecific whole antibodies may be made by knobs-into-holes engineering [Ridgeway et al., Protein Eng., 1996. 9, 616-621].

It will be appreciated that references to "an IL-13 antibody" include references to a whole antibody or antibody fragment which is capable of neutralising naturally occurring IL-13 at a concentration of less than 500 nM by following the assays as set forth in Examples 2-10 and 25 of WO 2005/007699.

Preferably, the IL-13 antibody neutralises naturally occurring IL-13 with a potency that is equal to or better than the potency of an IL-13 antigen binding site formed by BAK502G9 VH domain (SEQ ID NO: 15 in WO 2005/007699 (also published as U.S. Patent Application Publication No. 2007/0128192, now U.S. Pat. No. 7,829,090, herein incorporated by reference in its entirety) and the BAK502G9 VL domain (SEQ ID NO: 16 in WO 2005/007699 (also published as U.S. Patent Application Publication No. 2007/0128192, now U.S. Pat. No. 7,829,090, herein incorporated by reference in its entirety).

Preferably, the IL-13 antibody is a monoclonal IL-13 antibody, more preferably a human IL-13 monoclonal antibody.

A particularly preferred IL-13 antibody is one selected from those described in WO 2003/035847, WO 2003/086451, WO 2005/007699 or WO 2005/081873.

For example, in one particularly preferred embodiment, the IL-13 antibody is BAK278D6 HCDR1-3 and LCDR1-3 (SEQ ID NOS: 1-6 in WO 2005/007699 (also published as U.S. Patent Application Publication No. 2007/0128192, now U.S. Pat. No. 7,829,090, herein incorporated by reference in its entirety), respectively). A set of CDR's with the BAK278D6 set of CDR's, BAK278D6 set of HCDR's or BAK278D6 LCDR's, or one or two substitutions therein, is said to be of the BAK278D6 lineage.

In a further particularly preferred embodiment, the IL-13 antibody is BAK502G9 HCDR1-3 and LCDR1-3 (SEQ ID NOS: 7-12 in WO 2005/007699 (also published as U.S. Patent Application Publication No. 2007/0128192, now U.S. Pat. No. 7,829,090, herein incorporated by reference in its entirety), respectively).

In a yet further particularly preferred embodiment, the IL-13 antibody is BAK1111D10 HCDR1-3 and LCDR1-3 (SEQ ID NOS: 91-96 in WO 2005/007699 (also published as U.S. Patent Application Publication No. 2007/0128192, now U.S. Pat. No. 7,829,090, herein incorporated by reference in its entirety), respectively).

In a yet further particularly preferred embodiment, the IL-13 antibody is BAK1167F2 HCDR1-3 and LCDR1-3 (SEQ ID NOS: 61-66 in WO 2005/007699 (also published as U.S. Patent Application Publication No. 2007/0128192, now U.S. Pat. No. 7,829,090, herein incorporated by reference in its entirety), respectively).

In a yet further particularly preferred embodiment, the IL-13 antibody is BAK1183H4 HCDR1-3 and LCDR1-3 (SEQ ID NOS: 97-102 in WO 2005/007699 (also published as U.S. Patent Application Publication No. 2007/0128192, now U.S. Pat. No. 7,829,090, herein incorporated by reference in its entirety), respectively).

The relevant set of CDR's is provided within antibody framework regions or other protein scaffolds, e.g. fibronectin or cytochrome B [Koide et al., J. Mol. Biol. 1998. 284, 1141-1151; Nygren et al., Current Opinion in Structural Biology, 1997. 7, 463-469]. Preferably antibody framework regions are employed, and where they are employed they are preferably germline, more preferably the antibody framework region for the heavy chain may be DP14 from the VH1 family. The preferred framework region for the light chain may be λ3-3H. For the BAK502G9 set of CDR's it is preferred that the antibody framework regions are for VH FR1-3, SEQ ID NOS: 27-29 in WO 2005/007699, respectively and for light chain FR1-3, SEQ ID NOS: 30-32 in WO 2005/007699, respectively. In a preferred embodiment, a VH domain is provided with the amino acid sequence of SEQ ID NO: 15 in WO 2005/007699, this being termed "BAK502G9 VH domain". In a further highly preferred embodiment, a VL domain is provided with the amino acid sequence of SEQ ID NO: 16 in WO 2005/007699, this being termed "BAK502G9 VL domain.

In a preferred embodiment, the IL-13 antibody cross reacts with cynomologous IL-13 and/or the IL-13 variant, Q130R.

Preferably, the IL-13 antibody is present within the pharmaceutical composition in an amount of between 1 and 200 mg/ml, more preferably 50 and 100 mg/ml, especially 50 mg/ml.

Preferably, the pharmaceutical composition is buffered to a pH of 5.2 to 5.7, most preferably 5.5±0.1. The selection of such a pH confers significant stability to the pharmaceutical composition. Examples of alternative buffers that control the pH in this range include succinate, gluconate, histidine, citrate, phosphate, glutaric, cacodylyte, sodium hydrogen maleate, tris-(hydroxylmethyl)aminomethane (Tris), 2-(N-morpholino)ethanesulphonic acid (MES), imidazole and other organic acid buffers.

Preferably, the buffer is acetate buffer, more preferably sodium acetate.

Preferably, the acetate buffer is present within the pharmaceutical composition in an amount of between 1 and 100 mM, more preferably 30 and 70 mM, especially 50 mM.

It will be appreciated that references to "pharmaceutically acceptable excipient" includes references to any excipient conventionally used in pharmaceutical compositions. Such excipients may typically include one or more surfactant, inorganic or organic salt, stabilizer, diluent, solubilizer, reducing agent, antioxidant, chelating agent, preservative and the like.

Examples of a typical surfactant include: nonionic surfactants (HLB 6 to 18) such as sorbitan fatty acid esters (e.g. sorbitan monocaprylate, sorbitan monolaurate, sorbitan monopalmitate), glycerine fatty acid esters (e.g. glycerine monocaprylate, glycerine monomyristate, glycerine monostearate), polyglycerine fatty acid esters (e.g. decaglyceryl monostearate, decaglyceryl distearate, decaglyceryl monolinoleate), polyoxyethylene sorbitan fatty acid esters (e.g. polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g. polyoxyethylene sorbitol tetrastearate, polyoxyethylene sorbitol tetraoleate), polyoxyethylene glycerine fatty acid esters (e.g. polyoxyethylene glyceryl monostearate), polyethylene glycol fatty acid esters (e.g. polyethylene glycol distearate), polyoxyethylene alkyl ethers (e.g. polyoxyethylene lauryl ether), polyoxyethylene polyoxypropylene alkyl ethers (e.g. polyoxyethylene polyoxypropylene glycol ether, polyoxyethylene polyoxypropylene propyl ether, polyoxyethylene polyoxypropylene cetyl ether), polyoxyethylene alkylphenyl ethers (e.g. polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g. polyoxyethylene sorbitol beeswax), polyoxyethylene lanolin derivatives (e.g. polyoxyethylene lanolin), and polyoxyethylene fatty acid amides (e.g. polyoxyethylene stearyl amide);

anionic surfactants such as $C_{10}$-$C_{18}$ alkyl sulfates salts (e.g. sodium cetyl sulfate, sodium lauryl sulfate, sodium oleyl sulfate), polyoxyethylene $C_{10}$-$C_{18}$ alkyl ether sulfates salts with an average of 2 to 4 moles of ethylene oxide (e.g. sodium polyoxyethylene lauryl sulfate), and $C_8$-$C_{18}$ alkyl sulfosuccinate ester salts (e.g. sodium lauryl sulfosuccinate ester); and natural surfactants such as lecithin, glycerophospholipid, sphingophospholipids (e.g. sphingomyelin), and sucrose esters of $C_{12}$-$C_{18}$ fatty acids.

Preferably, the surfactant is selected from polyoxyethylene sorbitan fatty acid esters. Particularly preferably the surfactant is Polysorbate 20, 21, 40, 60, 65, 80, 81 and 85, most preferably Polysorbate 20 and 80, especially Polysorbate 80.

Preferably, the surfactant is present within the pharmaceutical composition in an amount of between 0.001 and 0.1% (w/w), more preferably 0.005 and 0.05 (w/w), especially 0.01% (w/w).

Examples of a typical inorganic salt include: sodium chloride, potassium chloride, calcium chloride, sodium phosphate, sodium sulphate, ammonium sulphate, potassium phosphate and sodium bicarbonate or any other sodium, potassium or calcium salt. Preferably, the inorganic salt is sodium chloride.

Preferably, the inorganic salt is present within the pharmaceutical composition in an amount of between 10 and 200 mM, more preferably 60 and 130 mM, especially 85 mM.

Examples of a reducing agent include N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid.

Examples of an antioxidant include erythorbic acid, dibutylhydroxytoluene, butylhydroxyanisole, alpha-tocopherol, tocopherol acetate, L-ascorbic acid and a salt thereof, L-ascorbic acid palmitate, L-ascorbic acid stearate, sodium bisulfite, sodium sulfite, triamyl gallate and propyl gallate.

Examples of a chelating agent include disodium ethylenediaminetetraacetate (EDTA), sodium pyrophosphate and sodium metaphosphate.

Examples of a stabiliser include creatinine, an amino acid selected from histidine, alanine, glutamic acid, glycine, leucine, phenylalanine, methionine, isoleucine, proline, aspartic acid, arginine, lysine and threonine, a carbohydrate selected from sucrose, trehalose, sorbitol, xylitol and mannose, surfactants selected from polyethylene glycol (PEG; e.g. PEG3350 or PEG4000) or polyoxyethylene sorbitan fatty acid esters (e.g. Polysorbate 20 or Polysorbate 80), or any combination thereof.

In one preferred embodiment the stabiliser comprises a single carbohydrate as hereinbefore defined (e.g. trehalose).

In an alternatively preferred embodiment the stabilizer comprises an amino acid in combination with a carbohydrate (e.g. trehalose and alanine or trehalose, alanine and glycine).

In a further alternatively preferred embodiment the stabiliser comprises an amino acid in combination with a carbohydrate and a surfactant (e.g. trehalose, alanine and PEG3350 or trehalose, proline and PEG3350 or trehalose, alanine and Polysorbate 80 or trehalose, proline and Polysorbate 80 or trehalose, alanine, glycine and PEG3350 or trehalose, alanine, glycine and Polysorbate 80).

In a yet further alternatively preferred embodiment the stabiliser comprises an amino acid in combination with a surfactant (e.g. alanine and PEG3350 or alanine, glycine and PEG3350).

In a yet further alternatively preferred embodiment the stabiliser comprises a carbohydrate in combination with a surfactant (e.g. trehalose and PEG3350 or trehalose and Polysorbate 80).

Examples of a preservative include octadecyldimethylbenzyl ammonium chloride, hexamethonium chloride, benzalkonium chloride (a mixture of alkylbenzyldimethylammonium chlorides in which the alkyl groups are long-chain compounds), benzethonium chloride, aromatic alcohols such as phenol, butyl and benzyl alcohol, alkyl parabens such as methyl or propyl paraben, catechol, resorcinol, cyclohexanol, 3-pentanol, and m-cresol.

In a preferred embodiment of the invention, the pharmaceutical composition comprises an IL-13 antibody, a surfactant and an inorganic salt buffered to a pH of 5.5±0.1 with acetate buffer.

In a further preferred embodiment of the invention, the pharmaceutical composition comprises an IL-13 antibody, sodium chloride and Polysorbate 80 buffered to a pH of 5.5±0.1 with sodium acetate buffer.

In a yet further preferred embodiment of the invention, the pharmaceutical composition comprises 50 mg/ml of an IL-13 antibody, 85 mM sodium chloride and 0.01% (w/w) Polysorbate 80 buffered to a pH of 5.5±0.1 with 50 mM sodium acetate buffer.

According to a second aspect of the invention there is provided a process for purifying an IL-13 antibody which comprises one or more chromatographic separation steps wherein each of said separation steps comprises elution with an elution buffer comprising one or more pharmaceutically acceptable excipients buffered to a pH of 3.5-7.0 with acetate buffer.

Preferably, the one or more chromatographic separation steps are selected from affinity chromatography (e.g. Protein A or Protein G affinity chromatography), ion exchange chromatography (e.g. cation and anion exchange chromatography), hydrophobic interaction chromatography (e.g. phenyl chromatography), hydroxyapatite chromatography, size exclusion chromatography, immobilised metal affinity chromatography, hydrophilic interaction chromatography, thiophilic adsorption chromatography, euglobulin adsorption chromatography, dye ligand chromatography or immobilised boronate chromatography. Most preferably, chromatographic separation is performed by Protein A affinity chromatography followed by cation exchange chromatography (e.g. using an SP-sepharose matrix) followed by anion exchange chromatography (e.g. using a Q-sepharose matrix).

Preferably, the one or more pharmaceutically acceptable excipients comprises an inorganic salt such as sodium chloride.

Preferably, the inorganic salt is present within the elution buffer in an amount of between 10 and 200 mM, more preferably 60 and 130 mM, especially 85 mM.

Examples of alternative buffers that control the pH in the range of 3.5-7.0 include succinate, gluconate, histidine, citrate, phosphate and other organic acid buffers.

Preferably, the buffer is acetate buffer, more preferably sodium acetate.

Preferably, the acetate buffer is present within the elution buffer in an amount of between 1 and 100 mM, more preferably 30 and 70 mM, especially 50 mM.

Most preferably, the elution buffer comprises 50 mM sodium acetate and 85 mM sodium chloride buffered to pH 5.5±0.1.

A nucleic acid encoding any IL-13 antibody of the invention (e.g. CDR or set of CDR's or VH domain or VL domain or antibody antigen-binding site or antibody molecule, e.g. scFv or IgG4 as provided), may be expressed by culturing under appropriate conditions recombinant host cells containing said nucleic acid. Following production by expression a VH or VL domain, or specific binding member may be isolated and/or purified using any suitable technique, then used as appropriate.

Specific binding members, VH and/or VL domains, and encoding nucleic acid molecules and vectors may be provided isolated and/or purified, e.g. from their natural environment, in substantially pure or homogeneous form, or, in the case of nucleic acid, free or substantially free of nucleic acid or gene origin other than the sequence encoding a polypeptide with the required function. Nucleic acid may comprise DNA or RNA and may be wholly or partially synthetic.

Reference to a nucleotide sequence as set out herein encompasses a DNA molecule with the specified sequence, and encompasses an RNA molecule with the specified sequence in which U is substituted for T, unless context requires otherwise.

Systems for cloning and expression of a polypeptide in a variety of different host cells are well known. Suitable host cells include bacteria, mammalian cells, plant cells, yeast and baculovirus systems and transgenic plants and animals.

Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Preferably, said mammalian cell line is a myeloma cell culture such as e.g. NS0 cells [Galfre and Milstein Methods Enzymology, 1981. 73, 3]. Myeloma cells are plasmacytoma cells, i.e. cells of lymphoid cell lineage. An exemplary NS0 cell line is e.g. cell line ECACC No. 85110503, freely available from the European Collection of Cell Cultures (ECACC), Centre for Applied Microbiology & Research, Salisbury, Wiltshire, SP4 0JG, United Kingdom. NS0 have been found able to give rise to extremely high product yields, in particular if used for production of recombinant antibodies.

An alternatively preferred mammalian cell line is Chinese hamster ovary (CHO) cells. These may be dihydrofolate reductase (dhfr) deficient and so dependent on thymidine and hypoxanthine for growth [PNAS, 1990. 77, 4216-4220]. The parental dhfr CHO cell line is transfected with the antibody gene and dhfr gene which enables selection of CHO cell transformants of dhfr positive phenotype. Selection is carried out by culturing the colonies on media devoid of thymidine and hypoxanthine, the absence of which prevents untransformed cells from growing and transformed cells from resalvaging the folate pathway and thereby bypassing the selection system. These transformants usually express low levels of the product gene by virtue of co-integration of both transfected genes. The expression levels of the antibody gene may be increased by amplification using methotrexate (MTX). This drug is a direct inhibitor of the dhfr enzyme and allows isolation of resistant colonies which amplify their dhfr gene copy number sufficiently to survive under these conditions. Since the dhfr and antibody genes are more closely linked in the original transformants, there is usually concomitant amplification, and therefore increased expression of the desired antibody gene.

Another selection system for use with CHO or myeloma cells is the glutamine synthetase (GS) amplification system described in WO 87/04462. This system involves the transfection of a cell with a gene encoding the GS enzyme and the desired antibody gene. Cells are then selected which grow in glutamine free medium. These selected clones are then subjected to inhibition of the GS enzyme using methionine sulphoximine (MSX). The cells, in order to survive, will amplify the GS gene with concomitant amplification of the gene encoding the antibody.

The expression of antibodies and antibody fragments in prokaryotic cells such as E. coli is well established in the art. For a review, see for example Pluckthun, A. Bio/Technology 1991. 9, 545-551. Expression in eukaryotic cells in culture is also available to those skilled in the art as an option for production of a specific binding member for example [Chadd, H. E. and Chamow, S. M., Current Opinion in Biotechnology 2001. 12, 188-194; Andersen, D. C. and Krummen, L. Current Opinion in Biotechnology 2002. 13, 117; Larrick, J. W. and Thomas, D. W. Current opinion in Biotechnology 2001. 12, 411-418].

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 3rd edition, Sambrook and Russell, 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1988, Short Protocols in Molecular Biology: A Compendium of Methods from Current Protocols in Molecular Biology, Ausubel et al. eds., John Wiley & Sons, 4th edition 1999. The disclosures of Sambrook et al. and Ausubel et al. (both) are incorporated herein by reference.

Introduction of a nucleic acid into a host cell may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome [Csonka, E. et al., Journal of Cell Science, 200. 113, 3207-3216; Vanderbyl, S. et al., Molecular Therapy, 2002. 5 (5), 10]. Incorporation may be either by random or targeted integration of one or more copies at single or multiple loci. For bacterial cells, suitable techniques may include calcium chloride transformation, electroporation and infection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell.

Integration may be promoted by inclusion of sequences which promote recombination with the genome, in accordance with standard techniques.

According to a third aspect of the invention there is provided a use of a pharmaceutical antibody composition as defined herein in the manufacture of a medicament for the treatment of an IL-13 related disorder.

Preferably, the IL-13 related disorder is selected from asthma, atopic dermatitis, allergic rhinitis, fibrosis, chronic obstructive pulmonary disease, scleroderma, inflammatory bowel disease and Hodgkin's lymphoma. The composition of the invention may also be used in the treatment of tumours and viral infections as IL-13 antibodies will inhibit IL-13 mediated immunosuppression. Most preferably, the IL-13 related disorder is asthma.

The invention further provides a method of treatment or prophylaxis of an IL-related disorder which comprises administering to the sufferer a therapeutically effective amount of a pharmaceutical antibody composition as defined herein.

The invention further provides a pharmaceutical antibody composition as defined herein for use in the treatment of an IL-13 related disorder.

The pharmaceutical composition of the invention may be a liquid formulation or a lyophilized formulation which is reconstituted before use. As excipients for a lyophilized formulation, for example, sugar alcohols or saccharides (e.g. mannitol or glucose) may be used. In the case of a liquid formulation, the pharmaceutical composition of the invention is usually provided in the form of containers with defined volume, including sealed and sterilized plastic or glass vials, ampoules and syringes, as well as in the form of large volume containers like bottles. Preferably, the composition of the invention is a liquid formulation.

The pharmaceutical composition of the invention may be administered orally, by injection (for example, subcutaneously, intravenously, intraperitoneal or intramuscularly), by inhalation, or topically (for example intraocular, intranasal, rectal, into wounds, on skin). The route of administration can be determined by the physicochemical characteristics of the treatment, by special considerations for the disease or by the requirement to optimise efficacy or to minimise side-effects.

Preferably, the composition of the invention is administered by subcutaneous injection. It is envisaged that treatment will not be restricted to use in the clinic. Therefore, subcutaneous injection using a needle free device may also be preferred.

In accordance with the invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; [Ledermann, J. A. et al., Int. J. Cancer, 1999. 47, 659-664; Bagshawe, K. D. et al., Antibody, Immunoconjugates and Radiopharmaceuticals, 1991. 4, 915-922].

The precise dose will depend upon a number of factors, including the size and location of the area to be treated, the precise nature of the antibody (e.g. whole antibody, fragment or diabody), and the nature of any detectable label or other molecule attached to the antibody. A typical antibody dose will be in the range 100 pg to 10 g for systemic applications, and 1 µg to 100 mg for topical applications.

Typically, the antibody will be a whole antibody, preferably the IgG4 isotype. A dose for a single treatment of an adult patient, may be proportionally adjusted for children and infants, and also adjusted for other antibody formats in proportion to molecular weight. Treatments may be repeated at daily, twice-weekly, weekly or monthly intervals, at the discretion of the physician. In preferred embodiments of the present invention, treatment is periodic, and the period between administrations is about two weeks or more, preferably about three weeks or more, more preferably about four weeks or more, or about once a month.

BRIEF DESCRIPTION OF THE FIGURES

FIG. 1 shows the results of SDS-PAGE analysis of samples at Day 1 of a 28 day stability assessment of the composition of the invention.

FIG. 2 shows the results of SDS-PAGE analysis of samples at Day 21 of a 28 day stability assessment of the composition of the invention.

FIG. 3 shows the results of GP-HPLC analysis of samples at Day 1 of a 28 day stability assessment of the composition of the invention.

FIG. 4 shows an amalgam of results obtained from GP-HPLC analysis of samples during a 28 day stability assessment of the composition of the invention at 2-8° C.

FIG. 5 shows an amalgam of results obtained from GP-HPLC analysis of samples during a 28 day stability assessment of the composition of the invention at 25° C.

FIG. 6 shows an amalgam of results obtained from GP-HPLC analysis of samples during a 28 day stability assessment of the composition when neutralised with differing buffers.

FIG. 7 shows the results of IEF analysis of samples at Day 28 of a 28 day stability assessment of the composition of the invention.

FIG. 8 shows the results of gel filtration HPLC analysis of a 12 month stability assessment of different formulations stored at −70° C.

FIG. 9 shows the results of gel filtration HPLC analysis of a 12 month stability assessment of different formulations stored at +5° C.

FIG. 10 shows the results of gel filtration HPLC analysis of a 12 month stability assessment of different formulations stored at +25° C.

FIG. 11 shows the results of gel filtration HPLC analysis of an 8 week stability assessment of different formulations stored at +37° C.

FIG. 12 shows the results of gel filtration HPLC analysis of a 5 day stability assessment of different formulations stored at +45° C.

FIG. 13 shows the results of reduced SDS-PAGE analysis at 0, 6 and 12 months during a 12 month stability assessment of different formulations when stored at −70° C.

FIG. 14 shows the percentage abundance of BAK502G9 heavy and light chains following reduced SDS-PAGE analysis in FIG. 13 when stored at −70° C.

FIG. 15 shows the results of reduced SDS-PAGE analysis at 0, 6 and 12 months during a 12 month stability assessment of different formulations when stored at +5° C.

FIG. 16 shows the percentage abundance of BAK502G9 heavy and light chains following reduced SDS-PAGE analysis in FIG. 15 when stored at +5° C.

FIG. 17 shows the results of reduced SDS-PAGE analysis at 0, 6 and 12 months during a 12 month stability assessment of different formulations when stored at +25° C.

FIG. 18 shows the percentage abundance of BAK502G9 heavy and light chains following reduced SDS-PAGE analysis in FIG. 17 when stored at +25° C.

FIG. 19 shows the results of reduced SDS-PAGE analysis at 0 and 8 weeks during an 8 week stability assessment of different formulations when stored at +37° C.

FIG. 20 shows the percentage abundance of BAK502G9 heavy and light chains following reduced SDS-PAGE analysis in FIG. 19 when stored at +37° C.

FIG. 21 shows the results of reduced SDS-PAGE analysis at 0 and 5 days during a 5 day stability assessment of different formulations when stored at +45° C.

FIG. 22 shows the percentage abundance of BAK502G9 heavy and light chains following reduced SDS-PAGE analysis in FIG. 21 when stored at +45° C.

FIG. 23 shows the results of non-reduced SDS-PAGE analysis at 0, 6 and 12 months during a 12 month stability assessment of different formulations when stored at −70° C.

FIG. 24 shows the percentage abundance of intact BAK502G9 monomer following non-reduced SDS-PAGE analysis in FIG. 23 when stored at −70° C.

FIG. 25 shows the results of non-reduced SDS-PAGE analysis at 0, 6 and 12 months during a 12 month stability assessment of different formulations when stored at +5° C.

FIG. 26 shows the percentage abundance of intact BAK502G9 monomer following non-reduced SDS-PAGE analysis in FIG. 25 when stored at +5° C.

FIG. 27 shows the results of non-reduced SDS-PAGE analysis at 0, 6 and 12 months during a 12 month stability assessment of different formulations when stored at +25° C.

FIG. 28 shows the percentage abundance of intact BAK502G9 monomer following non-reduced SDS-PAGE analysis in FIG. 27 when stored at +25° C.

FIG. 29 shows the results of non-reduced SDS-PAGE analysis at 0 and 8 weeks during an 8 week stability assessment of different formulations when stored at +37° C.

FIG. 30 shows the percentage abundance of intact BAK502G9 monomer following non-reduced SDS-PAGE analysis in FIG. 29 when stored at +37° C.

FIG. 31 shows the results of non-reduced SDS-PAGE analysis at 0 and 5 days during a 5 day stability assessment of different formulations when stored at +45° C.

FIG. 32 shows the percentage abundance of intact BAK502G9 monomer following non-reduced SDS-PAGE analysis in FIG. 31 when stored at +45° C.

The present invention will now be illustrated, merely by way of example, with reference to the following methods and examples.

EXAMPLE 1

Expression of BAK502G9

BAK502G9 was expressed in a GS NS0 cell line in an analogous manner to the procedures described in WO 87/04462 and WO 2004/076485 and yielded culture supernatant containing 598 mg/l BAK502G9 antibody.

EXAMPLE 2

Purification of BAK502G9

(a) rmp Protein A Sepharose Purification

The column used for the rmp Protein A Sepharose fast flow chromatography step was 2.6 cm diameter, packed in 0.9% w/v sodium chloride, to a bed height of 14.5 cm giving a column volume of 77 ml. Resin was sourced from GE Healthcare/Amersham Biosciences 17-5138. Chromatography was performed using an Amersham Biosciences P-50 pump, UV1 detector and flow cell. The column was cleaned with 6M guanidine hydrochloride prior to use.

The rmp Protein A Sepharose fast flow column was subsequently equilibrated with 350 ml phosphate buffered saline pH 7.2, following water wash and cleaning. 2.6 l culture supernatant was loaded directly onto the column at 200 cm/hour and room temperature.

The column was then washed with 567 ml phosphate buffered saline pH 7.2 followed by 568 ml 50 mM sodium acetate pH 5.55. BAK502G9 antibody was eluted from the column by washing with 380 ml 50 mM sodium acetate pH 3.75. Post elution the column was washed with 50 mM acetic acid pH 3.0. The elution peak was collected between 2% maximum UV deflection on the up and down slope of the peak. 1.5 g BAK502G9 antibody was recovered in 217 ml.

(b) Low pH Viral Inactivation

The rmp Protein A Sepharose fast flow eluate was adjusted to pH 3.70 with 173 ml 100 mM acetic acid. The adjusted eluate was then held for 60 minutes for viral inactivation. After this time the adjusted eluate was neutralised with 437 ml 50 mM sodium hydroxide to pH 5.50 and 0.22 μm filtered using a Millipore stericup (product number SCGPU11RE). 1.4 g BAK502G9 antibody was recovered in 823 ml.

(c) SP Sepharose Purification

The column used for the SP Sepharose fast flow chromatography step was 1.6 cm diameter, packed in phosphate buffered saline pH 7.2, to a bed height of 15.5 cm giving a column volume of 31 ml. Resin was sourced from GE Healthcare/Amersham Biosciences 17-0729. Chromatography was performed using an Amersham Biosciences P-50 pump, UV1 detector and flow cell. The column was cleaned with 0.5M sodium hydroxide prior to use.

The SP Sepharose fast flow column was subsequently equilibrated with 145 ml 50 mM sodium acetate pH 5.50, following water wash and cleaning.

400 ml BAK502G9 antibody as neutralised rmp Protein A eluate was loaded directly onto the column at 200 cm/hour and room temperature.

The column was then washed with 302 ml 50 mM sodium acetate+30 mM sodium chloride pH 5.50.

BAK502G9 antibody was eluted from the column by washing with 150 ml 50 mM sodium acetate+85 mM sodium chloride pH 5.50. Post elution the column was washed with 50 mM sodium acetate+2M sodium chloride pH 5.50.

The elution peak was collected between 2% maximum UV deflection on the up slope and 30% on the down slope of the peak. Eluate was 0.22 μm filtered using a Millipore steriflip (product number SCGPOO525). 0.67 g BAK502G9 antibody was recovered in 54 ml.

This process step was repeated with the remaining 392 ml BAK502G9 antibody as neutralised rmp Protein A eluate. A further 0.67 g BAK502G9 antibody was recovered in 54 ml. The two filtered SP Sepharose eluates were pooled prior to the next step.

(d) Q Sepharose Fast Flow Chromatography

The column used for the Q Sepharose fast flow chromatography step was 1.6 cm diameter, packed in phosphate buffered saline pH 7.2, to a bed height of 13.3 cm giving a column volume of 27 ml. Resin was sourced from GE Healthcare/Amersham Biosciences 17-0510. Chromatography was performed using an Amersham Biosciences P-50 pump, UV1 detector and flow cell. The column was cleaned with 0.5M sodium hydroxide prior to use.

The Q Sepharose fast flow column was subsequently equilibrated with 138 ml 50 mM sodium acetate+85 mM sodium chloride pH 5.50, following water wash and cleaning.

44 ml BAK502G9 antibody as SP Sepharose eluate was loaded directly onto the column at 200 cm/hour and room temperature.

Isocratic elution of the BAK502G9 antibody was undertaken by washing the column with 124 ml 50 mM sodium acetate+85 mM sodium chloride pH 5.50. Post elution the column was washed with 50 mM sodium acetate+2M sodium chloride pH 5.50.

The elution peak was collected between 2% maximum UV deflection on the up slope and 2% on the down slope of the peak. Eluate was 0.22 nm filtered using a Millipore stericup (product number SCGPU01RE). 0.52 g BAK502G9 antibody was recovered in 88 ml. This process step was repeated with the remaining 44 ml BAK502G9 antibody as SP Sepharose eluate. A further 0.54 g BAK502G9 antibody was recovered in 51 ml. The two filtered Q Sepharose eluates were then pooled.

(e) Concentration

The product was obtained in 50 mM sodium acetate+85 mM sodium chloride pH 5.50 and did not require diafiltration. 95.31 g BAK502G9 antibody as Q Sepharose eluate in 17.5 l was concentrated to 1.5 l. A Millipore Pellicon 2 TFF system and a 0.1 $M^2$ 30 KDa membrane (Millipore P2B030A01) were used to carry out the concentration. The BAK502G9 antibody was then recovered from the equipment, the equipment was then buffer flushed with 50 mM sodium acetate+85 mM sodium chloride pH 5.50. The concentrated antibody was then combined with the buffer flush. 1.67 ml 10% w/v Polysorbate 80 was added to the pool to give a final Polysorbate 80 concentration of 0.01% w/v. The pool was then 0.22 μm filtered. 91.6 g BAK502G9 antibody was recovered in 1.67 l.

(f) Materials Used

The chemicals used to prepare the above buffers were as follows:
Guanidine hydrochloride. Sigma Aldrich. G4505
Di sodium hydrogen orthophosphate. VWR. 1038349
Sodium di hydrogen orthophosphate. VWR. 102454R
Sodium acetate 3-hydrate. VWR. 102354X.
Sodium chloride. VWR. 10241AP.
Acetic acid. VWR. 10001CU.
Polysorbate 80. J. T. Baker. 7394.

EXAMPLE 3

28 Day Stability Analysis

Methodology rmp Protein A chromatography was performed as set out in Table 1 below:

TABLE 1

| Protein A Chromatography Parameters | |
|---|---|
| Matrix: | rmp Protein A Sepharose |
| Bed height: | 14.2 cm |
| Column diameter | 5.0 cm |
| Column Volume | 278 ml |
| Linear flow rate: | 150 cm/hr |
| Equilibration buffer & CV's: | Phosphate buffered saline, pH 7.2, 5 CV's |
| Load material: | Clarified culture harvest. |
| Load capacity (mg IgG/ml matrix): | 16.6 mg/ml matrix |
| Wash 1 buffer and CV's: | Phosphate buffered saline, pH 7.2, 7.5 CV's |
| Wash 2 buffer and CV's: | 50 mM sodium acetate, pH 5.50 ± 0.10, 7.5 CV's |
| Elution buffer: | 50 mM sodium acetate, pH 3.75 ± 0.10, 1.6 CV's |
| Strip/Clean buffer and CV's: | 50 mM sodium acetate, pH 3.0 ± 0.10, 2 CVs. |

1.6 CV of elution buffer was required to elute the peak and for the absorbance to return to <2% full scale deflection (AuFS). After this the buffer was changed to strip buffer.

Low pH virus inactivation was then performed using the Protein A eluate as set out in Table 2 below:

TABLE 2

| Low pH virus inactivation | |
|---|---|
| Start material: | Protein A Eluate |
| pH reduction: | To pH 3.70 |
| Buffer for reduction of pH: | 100 mM acetic acid |
| Rate of addition: | 8.6 ml/min (19.0 ml/min/l eluate) |
| Hold time at low pH: | 60 minutes post pH adjustment |
| Neutralisation post virus inactivation: | To pH 5.48 by the gradual addition of 100 mM sodium hydroxide. |
| Rate of addition: | 17.8 ml/min (39.3 ml/min/l eluate - adjusted for sampling) |
| Filtration post neutralisation: | Millipak 20 |

All samples were stored in 200 ml Hyclone BioProcess containers which are made of polyethylene with C-flex inlet and outlet tubing attached.

In addition, a 50 ml sample of virus inactivated Protein A eluate was neutralised with the original buffer (50 mM sodium hydroxide) and stored in a bioprocess container at 2 to 8° C. for twenty-eight days before analysis.

All samples were either stored in a class 100,000 cold room (2 to 8° C., monitored with chart recorder and alarm) or in a thermostatically controlled incubator set to 25° C., as appropriate.

There were five time points and two storage temperatures (2 to 8° C. and 25° C.) i.e. ten separate sampling points.

The filtered neutralised Protein A eluate was split into ten lots; five lots being stored at each of the temperatures. A further container of unfiltered, neutralised Protein A eluate was stored at 2 to 8° C.

To fill each bioprocess container, the neutralised Protein A eluate was pumped through 0.2 µm Millipak filter into a 200 ml bioprocess container. Each bioprocess container was filled with approximately 100 ml to mimic the ratio of product to surface contact envisaged for the final 2,000 l scale production.

One bioprocess container was used for sampling for each temperature and each time-point and care was taken not to leave material in the tubing during storage.

One bioprocess container from each temperature was removed on days 1, 3, 15, 21 and 28. The contents of each bioprocess container were allowed to reach room temperature prior to sampling.

Samples were taken into Bijoux containers or 50 ml Falcon tubes. The first few mls of sample were discarded as they may have had some contact with the tubing during storage.

Post sampling the containers containing the remaining material were frozen at −70° C.

The following analysis was carried out on the day of each time point and for each storage temperature to determine comparability of these samples to each other and the reference standard. A fresh vial of BAK502G9 standard was used at each time point for comparison to the stability study material. The reference was thawed at room temperature from −70° C. storage. It is known that multimer levels can be elevated shortly following thawing of this antibody, so the GP-HPLC analysis was carried out last.

(A) Turbidity Analysis

Turbidity was assessed as a measure of protein degradation over time and therefore serves as a useful stability assessment of the composition of the invention.

Turbidity was measured by taking the average absorbance of the sample between A340 and 360 nm (Eckhardt et al. 1993). This assay was carried out without further filtration.

Data obtained from the rmp Protein A chromatography are summarised in Table 3 and the chromatogram is shown in FIG. 1.

TABLE 3

| rmp Protein A chromatography data | |
|---|---|
| Step Details | Result |
| Column volume | 278 ml |
| Total load volume | 3204 ml |
| Total product loaded | 4620 mg |
| Eluate volume | 453 ml (1.6 CV) |
| Concentration of eluate | 8.42 mg/ml |
| pH on elution | 4.40 |
| Volume of 100 mM acetic acid added | 665 ml (2.4 CV) |
| Volume of 100 mM sodium hydroxide added | 838 ml (3.0 CV; 3.2 CV adjusted*) |
| Volume pre in process filtration | 1900 ml* (6.8 CV) |
| Concentration post in process filtration | 2.28 mg/ml |
| Total product post in process filtration | 4327 mg |

TABLE 3-continued rmp Protein A chromatography data

| Step Details | Result |
|---|---|
| Percentage recovery post in process filtration | 93.7% |

*50 ml removed from virus-inactivated eluate for adjustment with 50 mM sodium hydroxide. Final volume is post sampling.

rmp Protein A chromatography performed as expected generating volumes of buffers comparable to that seen at large scale. The neutralised eluate was visibly more turbid than is usually seen with eluate neutralised with 50 mM sodium hydroxide. During filtration in to bioprocess containers, precipitation began to be observed, this occurred within one hour of neutralisation. Turbidity was not assayed until after this time. Recovery was within the expected range post filtration.

All eluate samples were assayed for turbidity on day one. Filtered eluates stored at both temperatures were assayed for turbidity on days: one, three, fifteen, twenty-one and twenty-eight. In addition eluates stored unfiltered (adjusted with either 50 mM sodium hydroxide or 100 mM sodium hydroxide) were assayed for turbidity both pre and post filtration at day twenty-eight. The results of the turbidity analysis are shown in Table 4 where it can be seen that although there was a noticeable increase in turbidity of the day twenty-eight sample stored at 25° C., the samples were generally stable at 25° C. for at least 21 days.

TABLE 4

Turbidity measurements of process and stability study samples

| Sample | Ave Turbidity | Category |
|---|---|---|
| Unadjusted eluate | 0.0640 | Opalescent |
| Virus inactivated | 0.0247 | Slightly Opalescent |
| Neutralised pre filtration | 0.2856 | Cloudy |
| Filtered eluate | 0.0093 | Clear |

| | 2 to 8° C. | | 25° C. | |
|---|---|---|---|---|
| Day | Turbidity | Category | Turbidity | Category |
| Day one. | 0.0093 | Clear | 0.0132 | Clear |
| Day three. | 0.0115 | Clear | 0.0176 | Slightly Opalescent |
| Day fifteen. | 0.0208 | Slightly Opalescent | 0.0203 | Slightly Opalescent |
| Day twenty-one. | 0.0120 | Clear | 0.0202 | Slightly Opalescent |
| Day twenty-eight | 0.0140 | Clear | 0.0412 | Opalescent |

(B) Protein Concentration Analysis

IgG concentration was measured and calculated using absorbance at 280 nm and an extinction coefficient of $E_{1cm}^{0.1\%}=1.723$.

The eluates that were filtered at the time of neutralisation were not re-filtered prior to absorbance at 280 nm being measured for calculating protein concentrations. As the turbidities were all low it is believed this would not have affected the results. Absorbance at 280 nm was consistent between storage temperatures and time points which is shown in Table 5.

TABLE 5

Protein concentrations of eluate samples

| Sample: Filtered neutralised Protein A eluate neutralised with 100 mM sodium hydroxide | Protein concentration (mg/ml) Temperature | |
|---|---|---|
| Day: | 2 to 8° C. | 25° C. |
| One. | 2.28 | 2.28 |
| Three. | 2.29 | 2.29 |
| Fifteen. | 2.28 | 2.29 |
| Twenty-one. | 2.29 | 2.28 |
| Twenty-eight. | 2.28 | 2.26 |
| Twenty-eight. Re-filtered. | 2.29 | — |

(C) SDS-PAGE Analysis

Reduced and non-reduced SDS PAGE was run using 4 to 12% Bis-Tris NuPAGE gels. Gels were run using MES running buffer and stained with Pierce gel code blue.

SDS PAGE analysis demonstrated variations in levels of half antibody, but there is no apparent trend and it is likely this is within the variation of the assay (see FIGS. 1 and 2 and Tables 6 and 7). At day twenty-one, some additional minor bands were seen in the 25° C. sample. These bands were not seen at day twenty-eight. Therefore these may be at the limits of detection of the assay. These bands may correspond with the small additional peaks seen on GP-HPLC (see Example 3D).

Samples were not run at the end of the study, as it would not be possible to distinguish between differences that were present in the original sample or were a result of the longer storage. A freshly thawed vial of reference standard was run on each gel. This was comparable between the different time points indicating that analysis had performed as expected. It is also notable that the extra bands seen in the day twenty-one, 25° C. sample, were not seen in the reference standard or 2 to 8° C. sample, run on the same gel. For clarity, all bands in FIG. 2 are indicated with a circle.

TABLE 6

SDS PAGE densitometry results, reduced samples

| | | Percentage | | | |
|---|---|---|---|---|---|
| Day | Sample | Heavy Chain | Light Chain | Half antibody | Others |
| One. | Reference. | 61.1 | 37.2 | 1.7 | 0.0 |
| | 2 to 8° C. | 61.3 | 37.4 | 1.2 | 0.0 |
| | 25° C. | 61.5 | 37.5 | 1.0 | 0.0 |
| Three. | Reference. | 65.7 | 32.4 | 1.9 | 0.0 |
| | 2 to 8° C. | 64.4 | 33.4 | 2.1 | 0.0 |
| | 25° C. | 66.0 | 32.8 | 1.2 | 0.0 |
| Fifteen. | Reference. | 62.7 | 35.9 | 1.3 | 0.0 |
| | 2 to 8° C. | 62.3 | 37.3 | 0.4 | 0.0 |
| | 25° C. | 62.4 | 39.9 | 0.7 | 0.0 |
| Twenty-one. | Reference. | 58.2 | 39.5 | 2.3 | 0.0 |
| | 2 to 8° C. | 57.8 | 39.9 | 2.2 | 0.1 |
| | 25° C. | 55.9 | 40.0 | 2.5 | 1.6 |
| Twenty-eight. | Reference. | 64.4 | 33.7 | 1.9 | 0.0 |
| | 2 to 8° C. | 66.1 | 32.5 | 1.4 | 0.0 |
| | 25° C. | 61.2 | 35.2 | 1.5 | 0.0 |

TABLE 7

SDS PAGE densitometry results, non-reduced samples

| | | Percentage | | |
|---|---|---|---|---|
| Day | Sample | Whole antibody | Half antibody | Other |
| One. | Reference. | 83.2 | 16.8 | 0.0 |
| | 2 to 8° C. | 82.6 | 17.4 | 0.0 |
| | 25° C. | 83.7 | 16.3 | 0.0 |
| Three. | Reference. | 89.8 | 10.2 | 0.0 |
| | 2 to 8° C. | 87.1 | 12.9 | 0.0 |
| | 25° C. | 87.4 | 12.6 | 0.0 |
| Fifteen. | Reference. | 86.0 | 14.0 | 0.0 |
| | 2 to 8° C. | 84.6 | 15.4 | 0.0 |
| | 25° C. | 86.8 | 13.2 | 0.0 |
| Twenty-one. | Reference. | 82.5 | 17.4 | 0.0 |
| | 2 to 8° C. | 81.6 | 17.9 | 0.5 |
| | 25° C. | 82.5 | 15.7 | 1.8 |
| Twenty-eight. | Reference. | 87.1 | 12.9 | 0.0 |
| | 2 to 8° C. | 85.0 | 14.8 | 0.0 |
| | 25° C. | 87.9 | 11.3 | 0.0 |

(D) GP-HPLC Analysis

Samples were analysed using a TSK GS3000SW size exclusion column with 200 mM sodium phosphate and 0.05% sodium azide pH 7.0 as the mobile phase and detection at 280 nm.

All fractions from Protein A chromatography were assayed on day 1. Eluates stored at both temperatures were then assayed on days: one, three, fifteen, twenty-one and twenty-eight. Reference samples were also run at all time points. Eluates separately neutralised with either 100 mM sodium hydroxide or 50 mM sodium hydroxide on day one, but not filtered until day twenty-eight were assayed on day twenty-eight by GP-HPLC.

Chromatograms from GP-HPLC analysis day one are shown in FIG. 3. These are as expected the final eluate being >95% monomer, which meets the final specification for BAK502G9.

GP-HPLC analysis of samples throughout the course of the study revealed a slight increase in truncated (in particular a small peak eluting between 9.9 and 10.3 minutes) BAK502G9 at 25° C. (Table 8 and FIGS. 4 and 5). Levels of monomer were consistently between 97.0 and 98.2% over the whole study.

Eluates neutralised with 50 mM sodium hydroxide had higher levels of monomer (99.2% monomer) than eluate neutralised with 100 mM sodium hydroxide (97.4% monomer), both being higher than the required level of 95% monomer for final product (Table 9 and FIG. 6).

The results obtained from the automatic integration were found to be inaccurate, therefore, the GP-HPLC chromatograms were manually re-integrated.

TABLE 8

GP-HPLC of eluates stored at different temperatures

| | 2 to 8° C. (percentage) | | | 25° C. (percentage) | | |
|---|---|---|---|---|---|---|
| Day | Multimer | Monomer | Truncate | Multimer | Monomer | Truncate |
| 1 | 1.4 | 98.2 | 0.4 | 1.4 | 98.0 | 0.7 |
| 3 | 1.7 | 97.5 | 0.8 | 1.0 | 98.3 | 0.7 |
| 15 | 1.4 | 98.0 | 0.6 | 1.0 | 98.0 | 1.0 |
| 21 | 1.2 | 98.1 | 0.6 | 1.3 | 97.4 | 1.3 |
| 28 | 1.2 | 98.2 | 0.7 | 1.5 | 97.0 | 1.5 |

TABLE 9

GP-HPLC of eluates neutralised with either 100 mM or 50 mM sodium hydroxide

| Fraction | Multimer (%) | Monomer (%) | Truncate (%) |
|---|---|---|---|
| Eluate neutralised with 100 mM sodium hydroxide, filtered and assayed day 28 | 1.4 | 97.4 | 1.2 |
| Eluate neutralised with 50 mM sodium hydroxide, filtered and assayed day 28 | 0.3 | 99.2 | 0.5 |
| Filtered, eluate neutralised with 100 mM sodium hydroxide, assayed day 28 | 1.4 | 98.2 | 0.4 |

(E): IEF Analysis

Samples were analysed using Invitrogen pH 3 to 10 IEF gels, using Invitrogen buffers.

IEF analysis of BAK502G9 showed a consistent appearance throughout this study (FIG. 7). Three major bands and two minor bands between approximate pIs of 7.1 and 6.4 are seen.

(F): Endotoxin Analysis

Samples taken on day twenty-eight from both storage temperatures were assayed for endotoxin levels using a LAL assay.

Endotoxin levels in samples stored at both temperatures were low. This demonstrates there has been no contamination by gram-negative bacteria over the course of the study.

Eluate stored at 2 to 8° C.=0.87 EU/mg.

Eluate stored at 25° C.<0.44 EU/mg.

Summary of 28 Day Stability Analysis Results

BAK502G9 stored for up to fifteen days at 2 to 8° C. or 25° C. is equivalent in all the assays carried out in Example 3. After twenty-one days some minor differences are observed by SDS PAGE (Example 3C) and GP HPLC (Example 3D) analysis, but the product remains comparable up to twenty-eight days.

EXAMPLE 4

12 Month Stability Analysis

The 12 month stability analysis was performed in an analogous manner to that described for the 28 day stability analysis of Example 3.

The study was designed to investigate the stability of different concentrations of BAK502G9 when stored at different temperatures (e.g. −70, +5, +25, +37 and +45° C.). The differing formulations used in this analysis are set out in Table 10 below:

TABLE 10

Composition of formulations used in 12 month stability analysis

| Formulation | Nominal concentration (mg/ml) | Composition |
|---|---|---|
| Control (CF) | 10 | 50 mM sodium acetate/85 mM sodium chloride pH 5.5 |
| Test 1A (TF1A) | 50 | 50 mM sodium acetate/85 mM sodium chloride/0.01% Polysorbate 80 pH 5.5 |
| Test 1B (TF1B) | 100 | 50 mM sodium acetate/85 mM sodium chloride/0.01% Polysorbate 80 pH 5.5 |
| Test 1C (TF1C) | 150 | 50 mM sodium acetate/85 mM sodium chloride/0.01% Polysorbate 80 pH 5.5 |

Analysis of samples were taken at varying timepoints, for example, the formulations stored at −70, +5, +25° C. were measured at 0, 3, 6, 9 and 12 months, the formulations stored at +37° C. were measured at 0, 1, 2, 4 and 8 weeks and the formulations stored at +45° C. were measured at 0, 1, 2 and 5 days.

(A) pH Analysis pH was measured using a PHM220 pH meter (Radiometer Analytical) fitted with a small volume pH electrode (BDH) and the results of pH measurement of formulations CF, TF1A, TF1B and TF1C at each temperature are shown in Tables 11-15 below:

TABLE 11 pH after storage at −70° C.

| Time (months) | pH | | | |
| --- | --- | --- | --- | --- |
| | CF | TF1A | TF1B | TF1C |
| 0 | 5.67 | 5.52 | 5.51 | 5.54 |
| 3 | 5.47 | 5.48 | 5.48 | NT |
| 6 | 5.50 | 5.50 | 5.48 | NT |
| 9 | 5.56 | 5.55 | 5.57 | 5.58 |
| 12 | 5.46 | 5.47 | 5.46 | 5.46 |

TABLE 12 pH after storage at +5° C.

| Time (months) | pH | | | |
| --- | --- | --- | --- | --- |
| | CF | TF1A | TF1B | TF1C |
| 0 | 5.67 | 5.52 | 5.51 | 5.54 |
| 3 | 5.48 | 5.49 | 5.49 | NT |
| 6 | 5.49 | 5.49 | 5.49 | NT |
| 9 | 5.56 | 5.56 | 5.55 | 5.56 |
| 12 | 5.47 | 5.47 | 5.46 | 5.47 |

TABLE 13 pH after storage at +25° C.

| Time (months) | pH | | | |
| --- | --- | --- | --- | --- |
| | CF | TF1A | TF1B | TF1C |
| 0 | 5.67 | 5.52 | 5.51 | 5.54 |
| 3 | 5.49 | 5.50 | 5.51 | NT |
| 6 | 5.49 | 5.50 | 5.48 | NT |
| 9 | 5.53 | 5.53 | 5.55 | 5.58 |
| 12 | 5.49 | 5.49 | 5.48 | 5.48 |

TABLE 14 pH after storage at +37° C.

| Time (weeks) | pH | | | |
| --- | --- | --- | --- | --- |
| | CF | TF1A | TF1B | TF1C |
| 0 | 5.50 | 5.52 | 5.52 | 5.52 |
| 1 | 5.45 | 5.46 | 5.46 | NT |
| 2 | 5.45 | 5.45 | 5.47 | NT |
| 4 | 5.46 | 5.45 | 5.45 | NT |
| 8 | 5.45 | 5.45 | 5.45 | 5.46 |

TABLE 15 pH after storage at +45° C.

| Time (days) | pH | | | |
| --- | --- | --- | --- | --- |
| | CF | TF1A | TF1B | TF1C |
| 0 | 5.50 | 5.52 | 5.52 | 5.52 |
| 1 | 5.47 | 5.48 | 5.48 | NT |
| 2 | 5.47 | 5.47 | 5.46 | NT |
| 5 | 5.48 | 5.48 | 5.47 | 5.49 |

NT = not tested (B) Concentration Analysis

Samples were diluted to an appropriate level with the relevant buffer and their absorbance at 280 nm determined using an HP8453 UV/visible spectrophotometer (Agilent Technologies). Absorbance values were converted to BAK502G9 concentrations using the known extinction coefficient of 1.723. The results of absorbance measurement of formulations CF, TF1A, TF1B and TF1C at each temperature are shown in Tables 16-20 below:

TABLE 16

BAK502G9 concentration after storage at −70° C.

| Time (months) | Mean concentration ± SD$^a$ (mg/ml) | | | |
| --- | --- | --- | --- | --- |
| | CF | TF1A | TF1B | TF1C |
| 0 | 10.8 ± 0.1 | 48.9 ± 0.3 | 107.4 ± 0.9 | 147.7 ± 4.6 |
| 3 | 11.0 ± 0.1 | 52.4 ± 0.7 | 112.8 ± 0.6 | NT |
| 6 | 10.3 ± 0.1 | 46.4 ± 0.6 | 104.5 ± 2.1 | NT |
| 9 | 10.6 ± 0.2 | 46.9 ± 0.8 | 105.8 ± 0.7 | 151.8 ± 1.4 |
| 12 | 10.7 ± 0.1 | 50.9 ± 0.0 | 109.3 ± 0.3 | 152.7 |

TABLE 17

BAK502G9 concentration after storage at +5° C.

| Time (months) | Mean concentration ± SD$^a$ (mg/ml) | | | |
| --- | --- | --- | --- | --- |
| | CF | TF1A | TF1B | TF1C |
| 0 | 10.8 ± 0.1 | 48.9 ± 0.3 | 107.4 ± 0.9 | 147.7 ± 4.6 |
| 3 | 10.8 ± 0.2 | 51.4 ± 0.3 | 110.7 ± 0.3 | NT |
| 6 | 10.4 ± 0.2 | 46.4 ± 0.9 | 99.1 ± 0.9 | NT |
| 9 | 10.6 ± 0.1 | 46.6 ± 0.5 | 105.9 ± 0.9 | 150.2 ± 0.2 |
| 12 | 10.7 ± 0.1 | 50.5 ± 0.1 | 112.3 ± 0.4 | 156.1 ± 0.5 |

TABLE 18

BAK502G9 concentration after storage at +25° C.

| Time (months) | Mean concentration ± SD$^a$ (mg/ml) | | | |
| --- | --- | --- | --- | --- |
| | CF | TF1A | TF1B | TF1C |
| 0 | 10.8 ± 0.1 | 48.9 ± 0.3 | 107.4 ± 0.9 | 147.7 ± 4.6 |
| 3 | 10.8 ± 0.2 | 53.8 ± 0.4 | 116.2 ± 0.5 | NT |
| 6 | 10.4 ± 0.1 | 46.5 ± 0.4 | 102.9 ± 2.7 | NT |
| 9 | 10.6 ± 0.2 | 46.2 ± 0.9 | 106.3 ± 1.2 | 152.3 ± 1.9 |
| 12 | 10.2 ± 0.1 | 52.0 ± 0.9 | 110.8 ± 0.5 | 155.8 ± 1.3 |

TABLE 19

BAK502G9 concentration after storage at +37° C.

| | Mean concentration ± SD[a] (mg/ml) | | | |
|---|---|---|---|---|
| Time (weeks) | CF | TF1A | TF1B | TF1C |
| 0 | 10.4 ± 0.1 | 46.4 ± 0.4 | 98.6 ± 1.2 | 142.3 ± 0.8 |
| 1 | 11.1 ± 0.2 | 52.1 ± 0.7 | 112.1 ± 0.8 | NT |
| 2 | 11.0 ± 0.3 | 51.4 ± 1.3 | 118.7 ± 0.3 | NT |
| 4 | 10.9 ± 0.3 | 54.2 ± 0.4 | 120.6 ± 1.0 | NT |
| 8 | 11.0 ± 0.2 | 56.2 ± 1.9 | 117.2 ± 0.2 | 165.8 ± 1.1 |

TABLE 20

BAK502G9 concentration after storage at +45° C.

| | Mean concentration ± SD[a] (mg/ml) | | | |
|---|---|---|---|---|
| Time (days) | CF | TF1A | TF1B | TF1C |
| 0 | 10.4 ± 0.1 | 46.4 ± 0.4 | 98.6 ± 1.2 | 142.3 ± 0.8 |
| 1 | 10.6 ± 0.2 | 54.6 ± 1.7 | 120.4 ± 2.4 | NT |
| 2 | 10.7 ± 0.1 | 54.7 ± 1.4 | 124.9 ± 1.3 | NT |
| 5 | 10.6 ± 0.3 | 54.7 ± 2.0 | 122.2 ± 0.3 | 151.5 ± 1.6 |

[a] n = 3
NT = not tested (C) Gel Filtration HPLC Analysis

Gel filtration HPLC was performed on an HP1100 system (Agilent Technologies). A TSK-Gel 3000S column was equilibrated with 0.2M sodium phosphate pH7.5. Samples were diluted to 1 mg/ml with the relevant buffer and centrifuged at 13,000 rpm for 10 minutes to remove any particulate matter. 3×20 μl injections of each sample were made onto the column, which was run at a flow rate of 1 ml/min. A variable wavelength detector was used to monitor absorbance at 220 and 280 nm.

The results of gel filtration analysis of formulations CF, TF1A, TF1B and TF1C at each temperature are shown in FIGS. 8-12.

(D) Reduced SDS-PAGE Analysis

Samples were diluted to 1 mg/ml with the relevant buffer and 16.7 μl added to 12.5 μl of 4×LDS sample buffer (Invitrogen), 15.8 μl of Milli-Q water and 5 μl reducing agent (Invitrogen). The samples were heated at 95° C. for one minute and then placed on ice. 15 μl of each sample was loaded onto a 4-12% BisTris gel (Invitrogen) in a tank containing 1×MES SDS running buffer and the gel run for 35 minutes at a constant current of 500 mA. After electrophoresis the gel was removed from its casing, rinsed for 3×10 minutes with Milli-Q water, stained with Gelcode® Blue staining reagent (Pierce) for a minimum of one hour and then destained with Milli-Q water. The gel was photographed and analysed using a UVP GDS8000 gel documentation system. The relative abundance of BAK502G9 heavy and light chain in each sample was determined.

The results of reduced SDS-PAGE analysis of formulations CF, TF1A, TF1B and TF1C at each temperature are shown in FIGS. 13, 15, 17, 19 and 21. Measurements of abundance of BAK502G9 heavy and light chains at each temperature are also shown in FIGS. 14, 16, 18, 20 and 22.

(E) Non-Reduced SDS-PAGE Analysis

Samples were diluted to 1 mg/ml with the relevant buffer and 16.7 μl added to 25 μl of 2× non-reducing sample buffer (0.125M Tris pH6.8, 4% (w/v) SDS, 30% (v/v) glycerol, 0.004% (w/v) bromophenol blue), 3.3 μl of Milli-Q water and 5 μl 1M iodoacetamide. The samples were heated at 95° C. for one minute and then placed on ice. 15 μl of each sample was loaded onto a 4-12% BisTris gel (Invitrogen) in a tank containing 1×MES SDS running buffer and the gel run for 35 minutes at a constant current of 500 mA. After electrophoresis the gel was removed from its casing, rinsed for 3×10 minutes with Milli-Q water, stained with Gelcode® Blue staining reagent (Pierce) for a minimum of one hour and then destained with Milli-Q water. The gel was photographed and analysed using a UVP GDS8000 gel documentation system. The relative abundance of BAK502G9 monomer in each sample was determined.

The results of non-reduced SDS-PAGE analysis of formulations CF, TF1A, TF1B and TF1C at each temperature are shown in FIGS. 23, 25, 27, 29 and 31. Measurements of abundance of intact BAK502G9 monomer at each temperature are also shown in FIGS. 24, 26, 28, 30 and 32.

(F) Isoelectric Focusing Analysis

Prior to sample loading, the electrophoresis bed was cooled and a pH3-10 IEF gel (Cambrex) was prefocused for 10 minutes at 1 W, 2000V, 150 mA using an Apelex PS9009TX power pack. Samples were diluted to 1 mg/ml with the relevant buffer. A sample mask was placed on the surface of the gel and 5 μl of each sample was loaded. The gel was prefocused again and the sample mask removed. The gel was then focused for 60 minutes at 25 W, 1500V, 50 mA. After electrophoresis, the gel was fixed with 50% (v/v) methanol, 6% (w/v) trichloroacetic acid, 3.6% (w/v) 5-sulphosalicyclic acid for 30 minutes, then washed with water and dried in an oven at 40-50° C. for one hour. The gel was stained for 30 minutes using PhastGel Blue R (Pharmacia; one tablet dissolved in 60% (v/v) methanol), washed with Milli-Q water to remove excess stain and then destained for approximately 3 minutes with 9% (v/v) glacial acetic acid, 25% (v/v) ethanol solution. The gel was dried in an oven at 40-50° C. for one hour. The dried gel was photographed and analysed using a UVP GDS8000 gel documentation system. The number and pI range of the isoforms in each sample was determined and the results observed with formulations CF, TF1A, TF1B and TF1C at each temperature are shown in Tables 21-25 below:

TABLE 21 pI range and number of isoforms by IEF after storage at −70° C.

| | pI range (number of isoforms) | | | |
|---|---|---|---|---|
| Time (months) | CF | TF1A | TF1B | TF1C |
| 0 | 6.75-7.17 (4) | 6.74-7.17 (4) | 6.71-7.14 (4) | 6.69-7.10 (4) |
| 3 | 6.39-6.76 (4) | 6.39-6.74 (4) | 6.38-6.73 (4) | NT |
| 6 | 6.53-6.78 (4) | 6.63-6.85 (4) | 6.64-6.88 (4) | NT |
| 9 | 6.60-6.89 (4) | 6.60-6.88 (4) | 6.60-6.89 (4) | 6.61-6.89 (4) |
| 12 | 6.67-6.93 (4) | 6.64-6.91 (4) | 6.65-6.96 (4) | 6.69-6.99 (4) |

TABLE 22 pI range and number of isoforms by IEF after storage at +5° C.

| | pI range (number of isoforms) | | | |
|---|---|---|---|---|
| Time (months) | CF | TF1A | TF1B | TF1C |
| 0 | 6.75-7.17 (4) | 6.74-7.17 (4) | 6.71-7.14 (4) | 6.69-7.10 (4) |
| 3 | 6.59-6.85 (4) | 6.59-6.85 (4) | 6.59-6.86 (4) | NT |
| 6 | 6.66-6.91 (4) | 6.65-6.89 (4) | 6.68-6.95 (4) | NT |
| 9 | 6.66-6.94 (4) | 6.66-6.94 (4) | 6.64-6.90 (4) | 6.63-6.89 (4) |
| 12 | 6.62-6.91 (4) | 6.63-6.94 (4) | 6.62-6.92 (4) | 6.61-6.89 (4) |

TABLE 23 pI range and number of isoforms by IEF after storage at +25° C.

| Time (months) | pI range (number of isoforms) | | | |
|---|---|---|---|---|
| | CF | TF1A | TF1B | TF1C |
| 0 | 6.75-7.17 (4) | 6.74-7.17 (4) | 6.71-7.14 (4) | 6.69-7.10 (4) |
| 3 | 6.59-6.80 (4) | 6.62-6.83 (4) | 6.61-6.84 (4) | NT |
| 6 | 6.65-6.90 (4) | 6.69-6.98 (4) | 6.64-6.93 (4) | NT |
| 9 | 6.62-6.85 (4) | 6.61-6.85 (4) | 6.64-6.87 (4) | 6.64-6.89 (4) |
| 12 | 6.62-6.85 (4) | 6.61-6.86 (4) | 6.61-6.86 (4) | 6.62-6.88 (4) |

TABLE 24 pI range and number of isoforms by IEF after storage at +37° C.

| Time (weeks) | pI range (number of isoforms) | | | |
|---|---|---|---|---|
| | CF | TF1A | TF1B | TF1C |
| 0 | 6.65-6.95 (4) | 6.65-6.93 (4) | 6.63-6.92 (4) | 6.64-6.93 (4) |
| 1 | 6.47-6.77 (4) | 6.60-6.84 (4) | 6.63-6.88 (4) | NT |
| 2 | 6.57-6.78 (4) | 6.56-6.79 (4) | 6.58-6.82 (4) | NT |
| 4 | 6.62-6.84 (4) | 6.68-6.95 (4) | 6.69-6.98 (4) | NT |
| 8 | 6.61-6.86 (5) | 6.20-6.85 (7) | 6.28-6.89 (7) | 6.26-6.91 (7) |

TABLE 25 pI range and number of isoforms by IEF after storage at +45° C.

| Time (days) | pI range (number of isoforms) | | | |
|---|---|---|---|---|
| | CF | TF1A | TF1B | TF1C |
| 0 | 6.65-6.95 (4) | 6.65-6.93 (4) | 6.63-6.92 (4) | 6.64-6.93 (4) |
| 1 | 6.61-6.84 (4) | 6.64-6.88 (4) | 6.64-6.89 (4) | NT |
| 2 | 6.60.6.85 (4) | 6.56-6.78 (4) | 6.62-6.85 (4) | NT |
| 5 | 6.63-6.91 (4) | 6.65-6.95 (4) | 6.64-6.95 (4) | 6.64-6.93 (4) |

NT = not tested

Summary of Stability Analysis Results
Stability at −70° C.

Both CF and TF1A were stable for 12 months at −70° C. The analytical profiles were similar at 0 and 12 months except for the % intact IgG by non-reduced SDS-PAGE, which decreased from 95.9% at t=0 to 89.9% at 12 months for CF and from 96.2% at t=0 to 89.2% at 12 months for TF1A. By HPLC after 12 months, the percentage monomer for both CF and TF1A samples was 100%. Both CF and TF1A samples displayed 4 bands on IEF after 12 months. The results indicated that CF and TF1A are comparable at this temperature.

Stability at 5° C.

Both CF and TF1A were stable for 12 months at 5° C. The analytical profiles were similar at 0 and 12 months except for the % intact IgG by non-reduced SDS-PAGE, which decreased from 95.9% at t=0 to 89.5% at 12 months for CF and from 96.2% at t=0 to 88.9% at 12 months for TF1A. By HPLC after 12 months, the percentage monomer for both CF and TF1A samples was 100%. Both CF and TF1A samples displayed 4 bands on IEF after 12 months. The results indicated that CF and TF1A are comparable at this temperature.

Stability at 25° C.

Both CF and TF1A were stable for 12 months at 25° C. The % intact IgG by non-reduced SDS-PAGE decreased from 95.9% at t=0 to 89.1% at 12 months for CF and from 96.2% at t=0 to 87.5% at 12 months for TF1A. There is also a minor high molecular weight (>220 kDa) band in both formulations on the non-reduced SDS-PAGE gel that was not detected at t=0. By HPLC after 12 months, the percentage monomer for both CF and TF1A samples were 98.9 and 96.42%, respectively. Both CF and TF1A samples displayed 4 bands on IEF after 12 months. The results indicated that CF and TF1A are comparable at this temperature.

Stability at 37° C.

Both CF and TF1A were stable for 4 weeks at 37° C. but failed to meet the draft specification for some parameters after 8 weeks, namely purity by reduced SDS-PAGE (both formulations) and % monomer by GF-HPLC (TF1A only; borderline result). The results indicated that CF is more stable than TF1A at this temperature over an 8 week period.

Stability at 45° C.

Both CF and TF1A were stable for 5 days at 45° C. although there were slight changes in the analytical profiles after this time (some additional minor bands on SDS-PAGE and IEF gels). The results indicated that CF and TF1A are comparable at this temperature over a 5 day period.

Antibody Sequences disclosed in WO 2005/007699 (also published as U.S. Patent Application Publication No. 2007/0128192, now U.S. Pat. No. 7,829,090, herein incorporated by reference in its entirety) include:

BAK502G9 variable heavy domain (VH):
QVQLVQSGAEVKKPGASVKVSCKASGYTFTNYGLSWVRQAPGQGLEWMGWISAN NGDTNYGQEFQGRVTMTTDTSTSTAYMELRSLRSDDTAVYYCARDSSSSWARWFF DLWGRGTLVTVSS (SEQ ID NO:1)

BAK502G9 variable light domain (VL):
SYVLTQPPSVSVAPGKTARITCGGNIIGSKLVHWYQQKPGQAPVLVIYDDGDRPSGIP ERFSGSNSGNTATLTISRVEAGDEADYYC-QVWDTGSDPVVFGGGTKLTVL (SEQ ID NO:2)

BAK502G9 heavy chain complementarity determining regions 1-3 (HCDR1-3) and light chain complementarity determining regions 1-3 (LCDR1-3):
HCDR1: NYGLS (SEQ ID NO:3)
HCDR2: WISANNGDTNYGQEFQG (SEQ ID NO:4)
HCDR3: DSSSSWARWFFDL (SEQ ID NO:5)
LCDR1: GGNIIGSKLVH (SEQ ID NO:6)
LCDR2: DDGDRPS (SEQ ID NO:7)
LCDR3: QVWDTGSDPVV (SEQ ID NO:8)

BAK278D6 heavy chain complementarity determining regions 1-3 (HCDR1-3) and light chain complementarity determining regions 1-3 (LCDR1-3):
HCDR1: NYGLS (SEQ ID NO:9)
HCDR2: WISANNGDTNYGQEFQG (SEQ ID NO:10)
HCDR3: DSSSNWARWFFDL (SEQ ID NO:11)
LCDR1: GGNNIGSKLVH (SEQ ID NO:12)
LCDR2: DDGDRPS (SEQ ID NO:13)
LCDR3: QVWDTGSDPVV (SEQ ID NO:14)

BAK1111D10 heavy chain complementarity determining regions 1-3 (HCDR1-3) and light chain complementarity determining regions 1-3 (LCDR1-3):
HCDR1: NYGLS (SEQ ID NO:15)
HCDR2: WIATPDGQTSYGQEFQG (SEQ ID NO:16)
HCDR3: DSNSSWARWFFDL (SEQ ID NO:17)
LCDR1: GGNIIGSKLVH (SEQ ID NO:18)
LCDR2: DDGDRPS (SEQ ID NO:19)
LCDR3: QVWDTGSDPVV (SEQ ID NO:20)

BAK1167F2 heavy chain complementarity determining regions 1-3 (HCDR1-3) and light chain complementarity determining regions 1-3 (LCDR1-3):
HCDR1: QTGVS (SEQ ID NO:21)
HCDR2: WISANNGDTNYGQEFQG (SEQ ID NO:22)
HCDR3: DSSSSWARWFFDL (SEQ ID NO:23)
LCDR1: GGNIIGSKLVH (SEQ ID NO:24)

LCDR2: DDGDRPS (SEQ ID NO:25)
LCDR3: QVWDTGSDPVV (SEQ ID NO:26)
BAK1183H4 heavy chain complementarity determining regions 1-3 (HCDR1-3) and light chain complementarity determining regions 1-3 (LCDR1-3):
HCDR1: NYGLS (SEQ ID NO:27)
HCDR2: WINYDGGNTQYGQEFQG (SEQ ID NO:28)
HCDR3: DSSSSWARWFFDL (SEQ ID NO:29)
LCDR1: GGNIIGSKLVH (SEQ ID NO:30)
LCDR2: DDGDRPS (SEQ ID NO:31)
LCDR3: QVWDTGSDPVV (SEQ ID NO:32).

The invention claimed is:

1. A process for purifying an IL-13 antibody comprising more than one chromatographic separation steps, wherein each of said separation steps comprises elution with a single acetate buffer comprising 50 mM sodium acetate and 85 mM sodium chloride buffered to a pH of 3.5-7.0.

2. The process of claim 1, wherein the chromatographic separation steps are selected from the group consisting of affinity chromatography and ion exchange chromatography.

3. The process of claim 2, wherein the chromatographic separation is performed by Protein A affinity chromatography followed by cation exchange chromatography followed by anion exchange chromatography.

4. The process of any one of claims 1 to 3, wherein the elution buffer is buffered to pH 5.5±0.1.

5. The process of any one of claims 1 to 3, wherein the IL-13 antibody is a human monoclonal antibody.

6. The process of any one of claims 1 to 3, wherein the IL-13 antibody is selected from the group consisting of:
   (a) An antibody comprising a set of complementarity determining regions (CDRs) HCDR1, HCDR2, HCDR3, LCDR1, LCDR2 and LCDR3, wherein HCDR1 has the amino acid sequence of SEQ ID NO:9, HCDR2 has the amino acid sequence of SEQ ID NO:10, HCDR3 has the amino acid sequence of SEQ ID NO:11, LCDR1 has the amino acid sequence of SEQ ID NO:12, LCDR2 has the amino acid sequence of SEQ ID NO:13, and LCDR3 has the amino acid sequence of SEQ ID NO:14;
   (b) An antibody comprising a set of complementarity determining regions (CDRs) HCDR1, HCDR2, HCDR3, LCDR1, LCDR2 and LCDR3, wherein HCDR1 has the amino acid sequence of SEQ ID NO:3, HCDR2 has the amino acid sequence of SEQ ID NO:4, HCDR3 has the amino acid sequence of SEQ ID NO:5, LCDR1 has the amino acid sequence of SEQ ID NO:6, LCDR2 has the amino acid sequence of SEQ ID NO:7, and LCDR3 has the amino acid sequence of SEQ ID NO:8;
   (c) An antibody comprising a set of complementarity determining regions (CDRs) HCDR1, HCDR2, HCDR3, LCDR1, LCDR2 and LCDR3, wherein HCDR1 has the amino acid sequence of SEQ ID NO:15, HCDR2 has the amino acid sequence of SEQ ID NO:16, HCDR3 has the amino acid sequence of SEQ ID NO:17, LCDR1 has the amino acid sequence of SEQ ID NO:18, LCDR2 has the amino acid sequence of SEQ ID NO:19, and LCDR3 has the amino acid sequence of SEQ ID NO:20;
   (d) An antibody comprising a set of complementarity determining regions (CDRs) HCDR1, HCDR2, HCDR3, LCDR1, LCDR2 and LCDR3, wherein HCDR1 has the amino acid sequence of SEQ ID NO:21, HCDR2 has the amino acid sequence of SEQ ID NO:22, HCDR3 has the amino acid sequence of SEQ ID NO:23, LCDR1 has the amino acid sequence of SEQ ID NO:24, LCDR2 has the amino acid sequence of SEQ ID NO:25, and LCDR3 has the amino acid sequence of SEQ ID NO:26;
   (e) An antibody comprising a set of complementarity determining regions (CDRs) HCDR1, HCDR2, HCDR3, LCDR1, LCDR2 and LCDR3, wherein HCDR1 has the amino acid sequence of SEQ ID NO:27, HCDR2 has the amino acid sequence of SEQ ID NO:28, HCDR3 has the amino acid sequence of SEQ ID NO:29, LCDR1 has the amino acid sequence of SEQ ID NO:30, LCDR2 has the amino acid sequence of SEQ ID NO:31, and LCDR3 has the amino acid sequence of SEQ ID NO:32; and
   (f) An antibody comprising a heavy chain variable region (VH) having the amino acid sequence of SEQ ID NO:1, and a light chain variable region (VL) having the amino acid sequence of SEQ ID NO:2.

7. The process of claim 6, wherein the IL-13 antibody comprises a set of complementarity determining regions (CDRs) HCDR1, HCDR2, HCDR3, LCDR1, LCDR2 and LCDR3, wherein HCDR1 has the amino acid sequence of SEQ ID NO:3, HCDR2 has the amino acid sequence of SEQ ID NO:4, HCDR3 has the amino acid sequence of SEQ ID NO:5, LCDR1 has the amino acid sequence of SEQ ID NO:6, LCDR2 has the amino acid sequence of SEQ ID NO:7, and LCDR3 has the amino acid sequence of SEQ ID NO:8.

8. The process of claim 6, wherein the IL-13 antibody comprises a heavy chain variable region (VH) having the amino acid sequence of SEQ ID NO:1, and a light chain variable region (VL) having the amino acid sequence of SEQ ID NO:2.

9. The process of claim 6, wherein the IL-13 antibody is present after elution in an amount of about 50 mg/ml, about 100 mg/ml or about 150 mg/ml.

10. The process of claim 9, wherein the IL-13 antibody is present after elution in an amount of about 150 mg/ml.

11. The process of claim 4, wherein the IL-13 antibody comprises a set of complementarity determining regions (CDRs) HCDR1, HCDR2, HCDR3, LCDR1, LCDR2 and LCDR3, wherein HCDR1 has the amino acid sequence of SEQ ID NO:3, HCDR2 has the amino acid sequence of SEQ ID NO:4, HCDR3 has the amino acid sequence of SEQ ID NO:5, LCDR1 has the amino acid sequence of SEQ ID NO:6, LCDR2 has the amino acid sequence of SEQ ID NO:7, and LCDR3 has the amino acid sequence of SEQ ID NO:8.

12. The process of claim 11, wherein the IL-13 antibody comprises a heavy chain variable region (VH) having the amino acid sequence of SEQ ID NO:1, and a light chain variable region (VL) having the amino acid sequence of SEQ ID NO:2.

13. The process of claim 11, wherein the IL-13 antibody is present after elution in an amount of about 50 mg/ml, about 100 mg/ml or about 150 mg/ml.

14. The process of claim 11, wherein the IL-13 antibody is present after elution in an amount of about 150 mg/ml.

* * * * *

SEQUENCE LISTING

```
<160> NUMBER OF SEQ ID NOS: 32

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
            100                 105

<210> SEQ ID NO 3
```

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Tyr Gly Leu Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Ile Ser Ala Asn Asn Gly Asp Thr Asn Tyr Gly Gln Glu Phe Gln
1               5                   10                  15

Gly

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ser Ser Ser Ser Trp Ala Arg Trp Phe Phe Asp Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Asn Ile Ile Gly Ser Lys Leu Val His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Asp Gly Asp Arg Pro Ser
1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 8

Gln Val Trp Asp Thr Gly Ser Asp Pro Val Val
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Tyr Gly Leu Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Ile Ser Ala Asn Asn Gly Asp Thr Asn Tyr Gly Gln Glu Phe Gln
1               5                   10                  15

Gly

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ser Ser Ser Asn Trp Ala Arg Trp Phe Phe Asp Leu
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Asn Asn Ile Gly Ser Lys Leu Val His
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Asp Gly Asp Arg Pro Ser
1               5

<210> SEQ ID NO 14
```

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Val Trp Asp Thr Gly Ser Asp Pro Val Val
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Tyr Gly Leu Ser
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ile Ala Thr Pro Asp Gly Gln Thr Ser Tyr Gly Gln Glu Phe Gln
1               5                   10                  15

Gly

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ser Asn Ser Ser Trp Ala Arg Trp Phe Phe Asp Leu
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Asn Ile Ile Gly Ser Lys Leu Val His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 19

Asp Asp Gly Asp Arg Pro Ser
1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Val Trp Asp Thr Gly Ser Asp Pro Val Val
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Thr Gly Val Ser
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Ile Ser Ala Asn Asn Gly Asp Thr Asn Tyr Gly Gln Glu Phe Gln
1               5                   10                  15

Gly

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Ser Ser Ser Ser Trp Ala Arg Trp Phe Phe Asp Leu
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Asn Ile Ile Gly Ser Lys Leu Val His
1               5                   10

<210> SEQ ID NO 25
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Gly Asp Arg Pro Ser
1               5

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Val Trp Asp Thr Gly Ser Asp Pro Val Val
1               5                   10

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Tyr Gly Leu Ser
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Ile Asn Tyr Asp Gly Gly Asn Thr Gln Tyr Gly Gln Glu Phe Gln
1               5                   10                  15

Gly

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Ser Ser Ser Ser Trp Ala Arg Trp Phe Phe Asp Leu
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Gly Gly Asn Ile Ile Gly Ser Lys Leu Val His
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Asp Gly Asp Arg Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Val Trp Asp Thr Gly Ser Asp Pro Val Val
1               5                   10
```